(12) United States Patent
Tanaka et al.

(10) Patent No.: US 11,134,972 B2
(45) Date of Patent: Oct. 5, 2021

(54) TREATMENT TOOL

(71) Applicant: Olympus Corporation, Hachioji (JP)

(72) Inventors: Kazuhiro Tanaka, Hachioji (JP); Yusuke Takei, Hino (JP); Ojiro Kitamura, Hachioji (JP); Akinori Kobayashi, Hino (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 256 days.

(21) Appl. No.: 16/220,010

(22) Filed: Dec. 14, 2018

(65) Prior Publication Data
US 2019/0117248 A1 Apr. 25, 2019

Related U.S. Application Data

(63) Continuation of application No. PCT/JP2016/068289, filed on Jun. 20, 2016.

(51) Int. Cl.
*A61B 17/29* (2006.01)
*A61B 17/068* (2006.01)
(Continued)

(52) U.S. Cl.
CPC ........ *A61B 17/2909* (2013.01); *A61B 17/068* (2013.01); *A61B 17/3201* (2013.01);
(Continued)

(58) Field of Classification Search
CPC .... A61B 2017/2946; A61B 2017/2929; A61B 2017/2903; A61B 17/2909; A61B 2017/2927; A61B 17/2841
See application file for complete search history.

(56) References Cited

U.S. PATENT DOCUMENTS 5,383,888 A 1/1995 Zvenyatsky et al.
5,456,695 A * 10/1995 Herve Dallemagne .....................
A61B 17/0218
606/198

(Continued)

FOREIGN PATENT DOCUMENTS

CN 204106087 U 1/2015
JP H07501965 3/1995
(Continued)

OTHER PUBLICATIONS

International Search Report and Written Opinion from corresponding International Application No. PCT/JP2016/068289, dated Aug. 16, 2016.

(Continued)

*Primary Examiner* — Darwin P Erezo
*Assistant Examiner* — Brigid K Byrd
(74) *Attorney, Agent, or Firm* — Oliff PLC

(57) ABSTRACT

A treatment tool includes a housing, a sheath rotatable around a predetermined axis of rotation with respect to the housing. An end effector is disposed on a distal-end portion of the sheath and rotatable in unison with the sheath around the axis of rotation. A locking member for restraining rotation of the sheath with respect to the housing by engaging the sheath. A manipulating member is mounted on the housing and moves with respect to the housing for causing the locking member and the sheath to switch between engaging and disengaging positions.

12 Claims, 9 Drawing Sheets

(51) Int. Cl.
  *A61B 17/3201* (2006.01)
  *A61B 17/00* (2006.01)
  *A61B 17/072* (2006.01)

(52) U.S. Cl.
  CPC .................. *A61B 17/07207* (2013.01); *A61B 2017/00314* (2013.01); *A61B 2017/00398* (2013.01); *A61B 2017/2919* (2013.01); *A61B 2017/2925* (2013.01); *A61B 2017/2927* (2013.01); *A61B 2017/2929* (2013.01); *A61B 2017/2946* (2013.01)

(56) References Cited

U.S. PATENT DOCUMENTS

| | | | | |
|---|---|---|---|---|
| 5,609,601 | A * | 3/1997 | Kolesa | A61B 17/29 606/170 |
| 2002/0082640 | A1 * | 6/2002 | Scholer | A61B 17/29 606/205 |
| 2006/0259070 | A1 * | 11/2006 | Livneh | A61B 17/2909 606/205 |
| 2007/0287993 | A1 | 12/2007 | Hinman et al. | |
| 2008/0154299 | A1 * | 6/2008 | Livneh | A61B 17/2909 606/205 |
| 2009/0114699 | A1 | 5/2009 | Viola | |
| 2010/0057121 | A1 * | 3/2010 | Piskun | A61B 17/3417 606/206 |
| 2012/0271347 | A1 | 10/2012 | Kaercher et al. | |
| 2014/0005663 | A1 | 1/2014 | Heard et al. | |

FOREIGN PATENT DOCUMENTS

| | | |
|---|---|---|
| JP | 09-000538 | 1/1997 |
| JP | 2008-539815 | 11/2008 |
| JP | 2013-176651 | 9/2013 |
| JP | 2014-008404 | 1/2014 |
| JP | 2014-205052 | 10/2014 |
| JP | 2015-080556 | 4/2015 |
| WO | 2006119139 | 11/2006 |

OTHER PUBLICATIONS

Office Action from corresponding International Application No. PCT/JP2016/068289, dated Sep. 10, 2019.

Nov. 30, 2020 Office Action issued in Chinese Patent Application No. 201680086970.5.

* cited by examiner

TREATMENT TOOL

CROSS-REFERENCE TO RELATED APPLICATION

This application is a continuation application of PCT Application No. PCT/JP2016/068289 filed on Jun. 20, 2016, which is hereby incorporated by reference in its entirety.

TECHNICAL FIELD

The present disclosure relates to a treatment tool for treating a treatment target with an end effector.

DESCRIPTION OF THE RELATED ART

U.S. Pat. No. 5,383,888 discloses a treatment tool having an end effector for treating a treatment target. The end effector is disposed on the distal end of a shaft. The shaft is coupled to a housing that can be held. When a handle is closed or opened with respect to a grip of the handle, the space between a pair of gripping members of the end effector is closed or opened. When the space between the gripping members is closed, a treatment target such as a living tissue or the like is gripped between the gripping members. A rotary member or rotary knob is mounted on the housing such that the rotary member is rotatable about the central axis of the shaft. When a manipulating force for rotating the rotary member is applied, the shaft and the end effector are rotated about the central axis of the shaft as a predetermined axis of rotation in unison with the rotary member with respect to the housing. The angular position of the end effector about the predetermined axis of rotation is thus changed. Furthermore, the end effector is bent with respect to the shaft, i.e., the central axis of the shaft, based on a manipulation of a bending manipulator or wing member on the housing.

BRIEF SUMMARY OF EMBODIMENTS

The present disclosure has been made in order to solve the problems described hereinbefore. It is an object of the present disclosure to provide a treatment tool which effectively prevents an end effector and a shaft or sheath from being rotated by a force acting on the end effector.

One aspect of the disclosed technology is directed to a treatment tool comprises a housing having a side surface facing in a widthwise direction thereof. An elongated member has respective proximal and distal ends. The elongated member is configured to be attached to the housing via the proximal end. The elongated member rotates around an axis of rotation with respect to the housing. An end effector is configured to be attached to the distal-end of the elongated member and rotates in unison with the elongated member around the axis of rotation. A locking member is configured to be attached to the housing so as to be engageable with the elongated member for restraining rotation of the elongated member around the axis of rotation with respect to the housing. A manipulating member is configured to be attached to the housing and being movable with respect to the housing in a first direction along the axis of rotation, a second direction toward the axis of rotation, or a third direction along the side surface and transverse to the axis of rotation, for switching from an engaged position to a disengaged position and vice versa. In the engaged position, the locking member and the elongated member engage with one another and in the disengaged position, the locking member and the elongated member disengage from one another.

Another aspect of the disclosed technology is directed to a treatment tool comprises a housing. An elongated member has respective proximal and distal ends. The elongated member is configured to be attached to the housing via the proximal end. The elongated member rotates around an axis of rotation with respect to the housing. An end effector is configured to be attached to the distal-end of the elongated member and rotates in unison with the elongated member around the axis. A locking member is configured to be attached to the housing so as to engage with the elongated member for restraining rotation of the elongated member around the axis. A manipulating member is attached to the housing and moves with respect to the housing for switching from an engaged position to a disengaged position and vice versa. The locking member and the elongated member are capable to engage with or to disengage from one another.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

Figure 1:
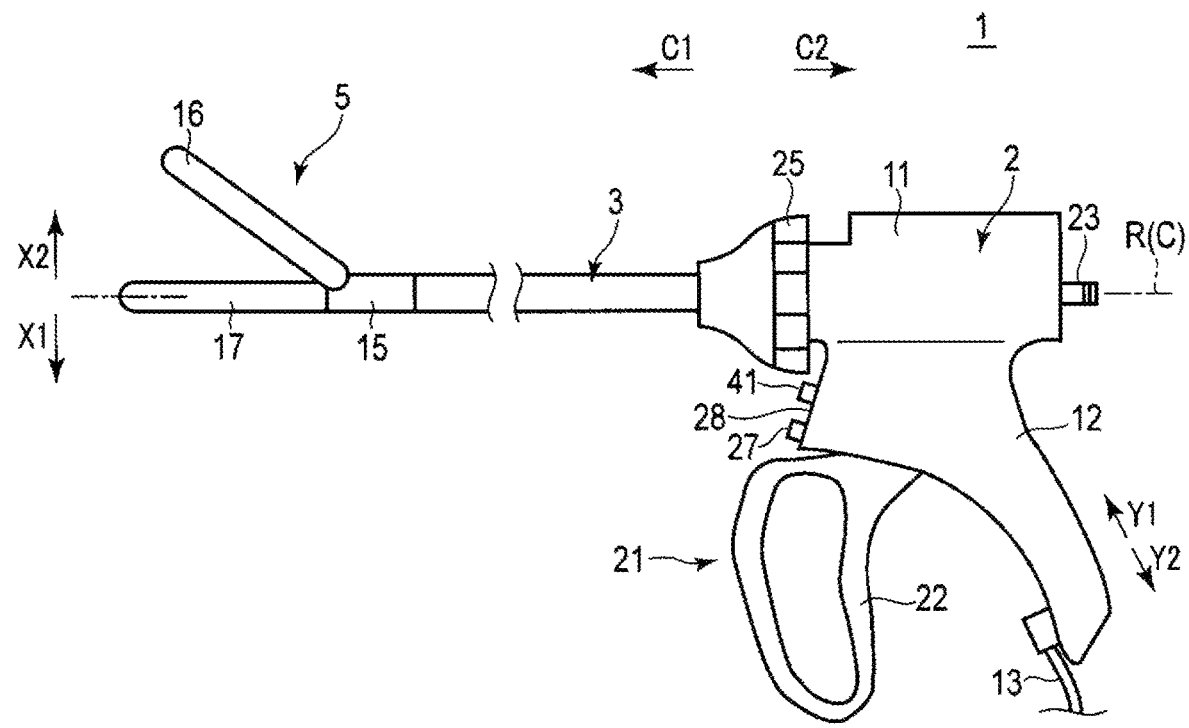
FIG. 1 is a schematic view of a treatment tool according to a first embodiment, as viewed from one side of a housing thereof in its widthwise directions.
Figure 2:
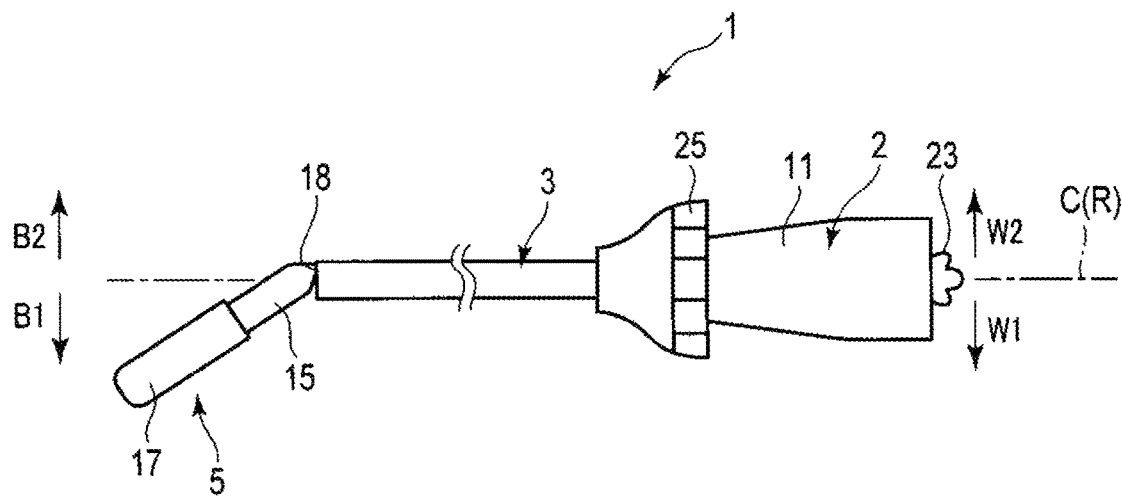
FIG. 2 is a schematic view of an end effector according to the first embodiment, as viewed from a side that is opposite the side where a grip is positioned with respect to a predetermined axis of rotation.

A first embodiment of the present disclosure will be described with reference to FIGS. 1 through 8. FIGS. 1 and 2 are views illustrating a treatment tool or gripping treatment tool 1 according to the present embodiment. As illustrated in FIGS. 1 and 2, the treatment tool 1 has a longitudinal axis C. Of the treatment tool 1, one side in a direction along the longitudinal axis C will be referred to as a distal-end side or arrow C1 side, and a side opposite the distal-end side will be referred to as a proximal-end side or arrow C2 side.

The treatment tool 1 includes a housing 2 that can be held, an elongated member defined by a shaft or sheath 3 coupled to a distal-end side of the housing 2, and an end effector 5 disposed on a distal-end portion of the shaft 3. The elongated member such as sheath or shaft 3 extends along the longitudinal axis from a proximal-end side to a distal-end side. The sheath or shaft 3 has a central axis that is substantially coaxial with the longitudinal axis C. The sheath or shaft 3 has a side extending toward the housing 2 as the proximal-end side and a side extending toward the end effector 5 as the distal-end side. The shaft 3 is rotatable about its central axis with respect to the housing 2. In other words, the central axis of the shaft 3 is used as an axis of rotation R about which the shaft 3 is rotatable about the housing 2.

The housing 2 includes a housing body 11 extending along the longitudinal axis C, i.e., the axis of rotation R of the sheath or shaft 3, and a grip or fixed handle 12 extending from the housing body 11 in directions transverse to the axis of rotation R, i.e., the directions indicated by the arrows Y1, Y2. The grip 12 is disposed in a region spaced from the axis of rotation R, i.e., the longitudinal axis C. A cable 13 has an end connected to the grip 12. The other end of the cable 13 is connected to an energy controller, not depicted. The directions that are transverse to the longitudinal axis C, i.e., the axis of rotation R, or substantially perpendicular thereto and that are also transverse to the direction in which the grip 12 extends, or substantially perpendicular thereto, will also be referred to as widthwise directions of the housing 2, i.e., the directions indicated by the arrows W1, W2. FIG. 1 is a view of the treatment tool 1 as viewed from one side in a widthwise direction of the housing 2, i.e., an arrow W1 side. FIG. 2 is a view of the treatment tool 1 as viewed from a side opposite the side where the grip 12 is positioned, with respect to the axis of rotation R, i.e., the longitudinal axis C.

The end effector 5 is rotatable in unison with the shaft 3 about the axis of rotation R with respect to the housing 2. The end effector 5 is also bendable with respect to the shaft 3, i.e., the axis of rotation R. When the end effector 5 rotates, the angular position of the end effector 5 about the axis of rotation R is changed. The directions in which the end effector 5 is bendable, i.e., the directions indicated by the arrows B1, B2, are transverse to the axis of rotation R or substantially perpendicular thereto. The end effector 5 includes a relay member 15, a first gripping member 16, and a second gripping member 17. The relay member 15 is attached to the distal end of the shaft 3 such that the relay member 15 is bendable with respect to the shaft 3. In other words, a bendable joint 18 is formed between the shaft 3 and the relay member 15. On the end effector 5, the space between the gripping members 16, 17 can selectively be opened and closed. The directions in which the gripping members 16, 17 are opened and closed, i.e., the directions indicated by the arrows X1, X2, are transverse to the axis of rotation R and are also transverse to the directions in which the end effector 5 is bendable.

According to an embodiment, one of the gripping members 16, 17 is integral with or fixed to the relay member 15. The other of the gripping members 16, 17 is angularly movably attached to the relay member 15. According to another embodiment, both the gripping members 16, 17 are angularly movably attached to the relay member 15. According to still another embodiment, a rod, not depicted, extends from within the relay member 15 toward the distal-end side, and a portion of the rod that projects from the relay member 15 toward the distal-end side is used as one of the gripping members 16, 17. The other of the gripping members 16, 17 is angularly movably attached to the relay member 15.

A handle or movable handle 21 is angularly movably mounted on the housing 2. When the handle 21 is angularly moved with respect to the housing 2, the handle 21 is opened or closed with respect to the grip 12. In other words, the handle 21 is openable and closable with respect to the grip 12. The handle 21 has a force applying portion 22 to which a manipulating force for opening or closing the handle 21 with respect to the grip 12 is applicable. According to the present embodiment, since the treatment tool 1 is pistol-shaped, the force applying portion 22 is positioned on one side with respect to the axis of rotation R, i.e., the longitudinal axis C, where the grip 12 is positioned, and on the distal-end side with respect to the grip 12. When the handle 21 is opened and closed with respect to the grip 12, the handle 21 is moved in directions substantially parallel to the longitudinal axis C. When a manipulating force is applied to the force applying portion 22, opening or closing the handle 21 with respect to the grip 12, a movable member, not depicted, extending in the shaft 3 moves along the longitudinal axis C, i.e., the axis of rotation R, with respect to the shaft 3 and the housing 2. At least one of the gripping members 16, 17 is now angularly moved with respect to the relay member 15, opening or closing the space between the gripping members 16, 17.

A bending dial 23 as a bending manipulation input portion is mounted on the housing 2. When a manipulation input is applied through the bending dial or bending manipulation input portion 23 by angularly moving the bending dial 23, for example, a bending wire, not depicted, extending in the shaft 3 moves along the longitudinal axis C, i.e., the axis of rotation R, with respect to the shaft 3 and the housing 2. The end effector 5 is now bent with respect to the shaft 3. The bending dial 23 may be rotatable in unison with the shaft 3 and the end effector 5 about the axis or rotation R with respect to the housing 2, or may not be rotatable in unison with the shaft 3 and the end effector 5 about the axis or rotation R. According to the present embodiment, the bending dial 23 is mounted on a proximal-end face of the housing body 11. However, the position of the bending dial 23 is not limited to the illustrated position. A bending manipulation input portion such as a bending dial 23 or the like may be mounted on an outer surface of the housing body 11 which faces a side opposite to the side where the grip 12 is positioned with respect to the axis of rotation R, i.e., the longitudinal axis C.

A rotary member or rotary knob 25 that is part of the shaft 3 is mounted on the distal-end side of the housing body 11. The shaft 3 is mounted on the housing 2 while being inserted from the distal-end side into the housing body 11. The rotary member 25 is fixed to the shaft 3 outside the housing 2. Therefore, the rotary member 25 is exposed outwardly of the housing. The rotary member 25 is rotatable in unison with the shaft 3 and the end effector 5 about the axis of rotation R with respect to the housing 2. The rotary member 25 is used as a rotational manipulation input member. A manipulating force tending to rotate the shaft 3 and the end effector 5 about the axis of rotation R is applied to the rotary member 25.

The housing 2 has, on an outer surface thereof, a mount surface 28 that faces the distal-end side at a position between the force applying portion 22 of the handle 21 and the rotary member 25. A manipulating button 27 is disposed on the mount surface 28. When the manipulating button 27 is pressed, a manipulation input is entered therefrom. For example, an energy controller detects that a manipulation input is entered from the manipulating button 27. According to an embodiment, when a manipulation input entered from the manipulating button 27 is detected, for example, either of a high-frequency current, ultrasonic vibrations, and heater heat is applied as treatment energy to a treatment target gripped between the gripping members 16, 17 in the same manner as known treatment tools. According to an embodiment, when a manipulation input entered from the manipulating button 27 is detected, an electric motor, not depicted, may be energized to stick a staple into the treatment target gripped between the gripping members 16, 17.

Figure 3:
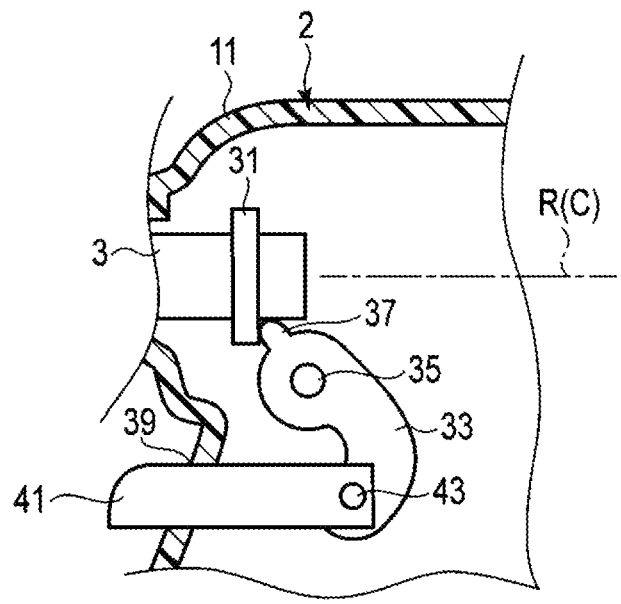
FIG. 3 is a schematic view of a locking member and a manipulating member that are disposed in a housing according to the first embodiment, as viewed from one side of the housing in its widthwise directions.

FIG. 3 is a view depicting the inside of the housing body 11. As illustrated in FIG. 3, the shaft 3 is inserted from the distal-end side into the housing body 11 of the housing 2. The shaft 3 has an engaging portion 31. The engaging portion 31 is fixed to an outer side of the shaft 3 in radial directions of the axis of rotation R. The engaging portion 31 projects toward outer circumferential sides from an outer circumferential surface of the shaft 3. The engaging portion 31 is positioned in the housing body 11. The engaging portion 31 rotates in unison with the shaft 3 about the axis of rotation R with respect to the housing 2. The engaging portion 31 has an outer circumferential surface formed to a serrated shape or gear shape.

The housing body 11 houses therein an angularly movable member or locking member 33 that is angularly movably attached to the housing body 11. The angularly movable member 33 is angularly movably attached to the housing body 11 by a support member 35 such as a pin or the like, for example. The support member 35 has a central axis extending along the widthwise directions of the housing 2. The angularly movable member 33 is angularly movable around the central axis of the support member 35 with respect to the housing body 11. The angularly movable member 33 has a protruding portion 37. When the angularly movable member 33 is angularly moved with respect to the housing body 11, the protruding portion 37 moves between a position in which it engages in a recess in the serrated shape or gear shape of the outer circumferential surface of the engaging portion 31 and a position in which it does not engage in a recess.

The mount surface 28 has an opening 39 defined therein. The opening 39 is a through hole extending through the mount surface 28 in directions along the longitudinal axis C. A manipulating lever or manipulating member 41 is disposed on the mount surface 28. The manipulating lever 41 extends along the axis of rotation R and projects from within the housing body 11 through the opening 39 toward the distal-end side.

The manipulating lever 41 has a proximal-end portion coupled to the angularly movable member 33 by a joint member 43 such as a pin or the like within the housing body 11. On the angularly movable member 33, the joint member 43 is positioned opposite the protruding portion 37 across the support member 35.

The manipulating lever 41 is movable with respect to the housing 2 in directions or first directions along the axis of rotation R. When the manipulating lever 41 is moved with respect to the housing 2, it applies an actuating force through the joint member 43 to the angularly movable member 33. Then, the angularly movable member 33 is angularly moved around the support member 35 with respect to the housing 2. When the angularly movable member 33 is angularly moved, the protruding portion 37 moves between the position in which it engages in a recess in the outer circumferential surface of the engaging portion 31 and the position in which it does not engage in a recess. When the protruding position 37 engages in a recess, the engaging portion 31 is prevented from rotating around the axis of rotation R. The engaging portion 31 rotates in unison with the shaft 3 around the axis of rotation R. The shaft 3 rotates in unison with the end effector 5 around the axis of rotation R. Therefore, when the engaging portion 31 is prevented from rotating around the axis of rotation R, the end effector 5 and the shaft 3 are prevented from rotating around the axis of rotation R.

According to the present embodiment, the angularly movable member 33 is used as a locking member for restraining or preventing the rotation of the shaft 3 around the axis of rotation R with respect to the housing 2 when the angularly movable member 33 engages the shaft 3 or the engaging portion 31. When the manipulating lever 41 moves in the directions or first directions along the axis of rotation R with respect to the housing 2, it switches between an engaged position in which the protruding portion 37 or the angularly movable member 33 and the engaging portion 31 or the shaft 3 engage each other and a disengaged position in which the protruding portion 37 or the angularly movable member 33 and the engaging portion 31 or the shaft 3 disengage each other. In other words, the manipulating lever 41 is a manipulating member movable between a locked position in which the locking member or the angularly movable member 33 and the shaft 3 engage each other and an unlocked position in which the locking member or the angularly movable member 33 and the engaging portion 31 or the shaft 3 disengage each other.

Next, operation and advantages of the treatment tool 1 according to the present embodiment will be described below. For treating a treatment target such as a living tissue or the like using the treatment tool 1, the operator holds the housing 2 with one hand thereof, i.e., the right hand or the left hand thereof, and inserts the end effector 5 into a body cavity such as an abdominal cavity or the like. With the manipulating lever 41 in the unlocked position, the operator rotates the rotary member 25 to rotate the shaft 3 and the end effector 5 around the axis of rotation R, and operates the bending dial 23 to bend the end effector 5 with respect to the shaft 3, thereby adjusting the position and posture of the end effector 5 in the body cavity. After having adjusted the position and posture of the end effector 5 in a manner to place the treatment target between the gripping members 16, 17, the operator closes the handle 21 with respect to the grip 12, closing the space between the gripping members 16, 17. The treatment target is now gripped between the gripping members 16, 17. With the treatment target being gripped, the operator presses the manipulating button 27 to enter a manipulation input, applying treatment energy such as a high-frequency current or the like to or sticking a staple into the treatment target gripped as described hereinbefore.

Figure 4:
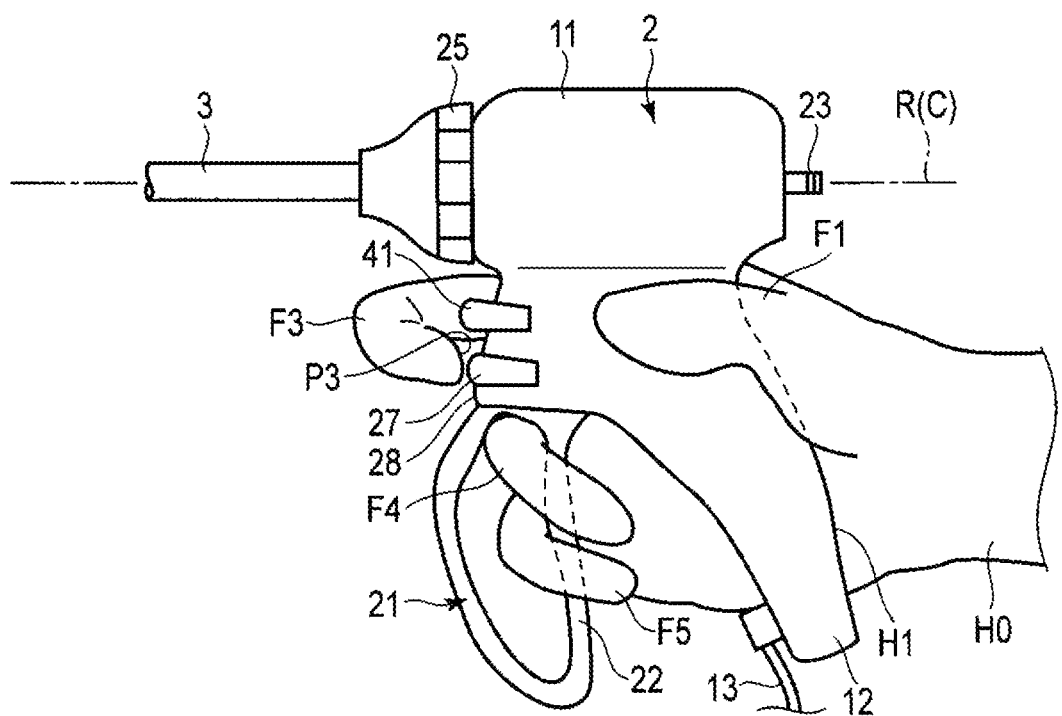
FIG. 4 is a schematic view of the housing according to the first embodiment that is held by a hand, as viewed from one side of the housing in its widthwise directions.
Figure 5:
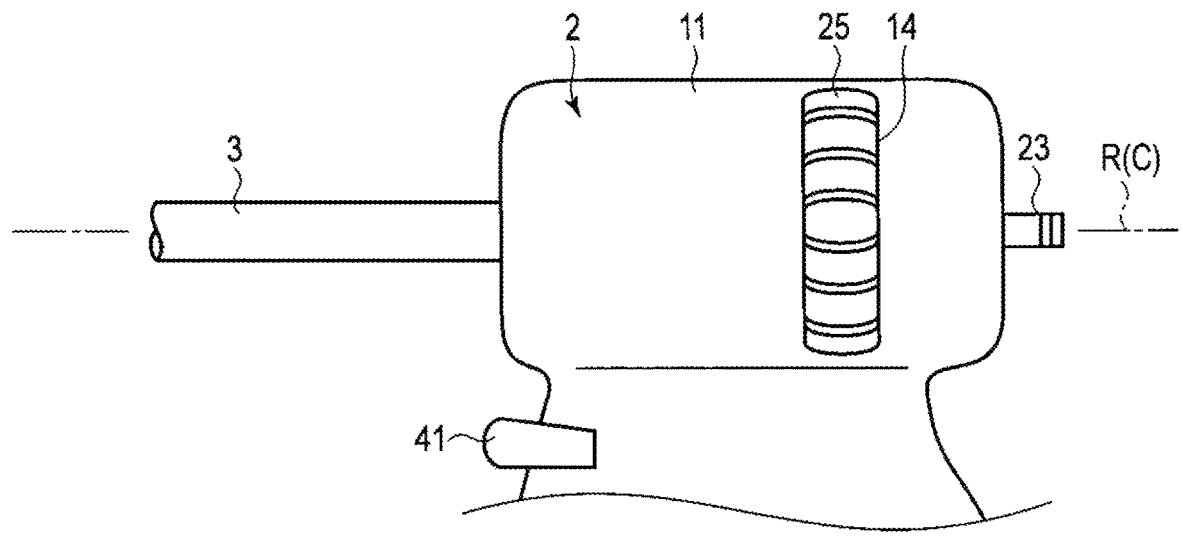
FIG. 5 is a schematic view of a treatment tool according to a first modification of the first embodiment, as viewed from one side of a housing thereof in its widthwise directions.

FIG. 4 is a view illustrating the housing 2 of the treatment tool 1 that is held by a hand H0, i.e., the right hand in FIG. 4. FIG. 4 is viewed from one side or the arrow W1 side in the widthwise directions of the housing 2. As illustrated in FIG. 4, while the housing 2 is being held by the hand H0, e.g., the right hand, the palm H1 and the thumb F1 are held against the grip 12 from the proximal-end side. The third finger F4 and the little finger F5 are placed on the force applying portion 22 of the handle 21, and the third finger F4 and/or the little finger F5 applies a manipulating force for opening or closing the handle 21 with respect to the grip 12 to the force applying portion 22. For bending the end effector 5 with respect to the shaft 3, the thumb F1 operates the bending dial or bending manipulation input portion 23. For adjusting the angular position of the end effector 5 around the axis of rotation R, the index finger F2, not depicted, operates the rotary member 25. The manipulating button 27 is pressed by the middle finger F3 or the index finger F2, so that the middle finger F3 or the index finger F2 enters a manipulation input from the manipulating button 27.

In a treatment using the treatment tool 1, a force may act on the end effector 5 while the end effector 5 is being bent with respect to the shaft 3 or the axis of rotation R. Since the force acts on the end effector 5 at a position spaced from the central axis of the shaft 3 or the axis of rotation R, an angular moment may be produced around the axis of rotation R, i.e., the central axis of the shaft 3, by the force acting on the end effector 5. When an angular moment is produced around the axis of rotation R by the force acting on the end effector 5, the operator brings the index finger F2 or the middle finger F3 into abutment against the distal-end portion of the manipulating lever 41 on the mount surface 28 of the housing 2. The operator then bends the index finger F2 or the middle finger F3 to press the manipulating lever 41 toward the proximal-end side. A manipulating force is now applied to the manipulating lever 41, moving the manipulating lever 41 to the unlocked position to the locked position. When the manipulating lever 41 is moved from the unlocked position to the locked position, the protruding portion 37 of the angularly movable member 33 and the engaging portion 31 of the shaft 3 switch from the disengaged position into the engaged position. In other words, the locking member or the angularly movable member 33 and the shaft 3 switch from the disengaged position into the engaged position. When the locking member and the shaft 3 switch from the disengaged position into the engaged position, the end effector 5 and the shaft 3 are prevented from rotating around the axis of rotation R, as described hereinbefore.

According to the present embodiment, even if an angular moment is produced around the axis of rotation R by a force acting on the end effector 5, the locking member or the angularly movable member 33 engages the shaft 3 due to a force applied from the index finger F2 or the middle finger F3 to the manipulating lever 41 as the manipulating member. The end effector 5 and the shaft 3 are effectively prevented from rotating around the axis of rotation R. The performance of a treatment that is performed while the treatment target is gripped between the gripping members 16, 17 is thus adequately maintained.

With a pistol-shaped treatment tool such as the treatment tool 1, while the housing 2 is being held by the hand H0, e.g., the right hand, the palm H1 and the thumb F1 are held against the grip 12 from the proximal-end side, and the third finger F4 and the little finger F5 are placed on the force applying portion 22 of the handle 21. At this time, the index finger F2 and the middle finger F3 extend from the palm H1 toward the distal-end side along the axis of rotation R. Therefore, the index finger F2 and the middle finger F3 can abut against the mount surface 28 from the distal-end side by being bent. The manipulating button 27 disposed on the mount surface 28 is pressed by the middle finger F3 or the index finger F2. According to the present embodiment, furthermore, the manipulating lever 41 is disposed on the mount surface 28. Therefore, while the housing 2 is being held by the hand H0, the manipulating lever or manipulating member 41 is positioned in a range where the index finger F2 and the middle finger F3 can abut against it. Consequently, the operator can operate the manipulating lever 41 to prevent the end effector 5 and the shaft 3 from rotating around the axis of rotation R, using only one of its hands.

Moreover, with a pistol-shaped treatment tool such as the treatment tool 1, while the housing 2 is being held by the hand H0, e.g., the right hand, the index finger F2 and the middle finger F3 extend from the palm H1 toward the distal-end side along the axis of rotation R. For applying a manipulating force to the manipulating lever 41 that is disposed on the mount surface 28 that faces the distal-end side, the operator bends the index finger F2 or the middle finger F3, bringing the pad P2, not depicted, of the index finger F2 or the pad P3 of the middle finger P3 into abutment against the manipulating lever 41. Therefore, it is easy for the index finger F2 or the middle finger F3 to apply a manipulating force to the manipulating lever 41 toward the proximal-end side. According to the present embodiment, when the manipulating lever 41 moves from a position on the distal-end side toward a position on the proximal-end side along the axis of rotation R, the angularly movable member 33 and the shaft 3 switch from the disengaged position to the engaged position. Therefore, it is easy for the index finger F2 or the middle finger F3 to apply a manipulating force for moving the manipulating lever 41 to the locked position to the manipulating lever 41 upon shifting to the engaged position. The operator can thus operate the manipulating lever 41 with one hand and with ease. Consequently, the end effector 5 and the shaft 3 are effectively prevented from rotating around the axis of rotation R.

While the manipulating lever 41 is being kept in the locked position, when a manipulating force is applied to the manipulating lever 41 in a direction along the axis of rotation R, the angularly movable member 33 and the shaft 3 are brought into the engaged position, preventing the end effector 5 and the shaft 3 from rotating around the axis of rotation R. If the finger, i.e., the index finger F2 and/or the middle finger F3, that has operated the manipulating lever 41 is then released from the manipulating lever 41, no manipulating force is applied to the manipulating lever 41. In other words, the manipulating lever 41 is freed from a manipulating force.

According to an embodiment, the manipulating lever 41 operates momentarily. In this case, while the manipulating lever 41 is being kept in the locked position, when the manipulating force applied to the manipulating lever 41 is released, the manipulating lever 41 is moved from the locked position to the unlocked position by a known actuating mechanism. As the manipulating lever 41 is moved from the locked position to the unlocked position, the angularly movable member 33 and the shaft 3 switch from the engaged position to the disengaged position. Therefore, the end effector 5 and the shaft 3 are released from the position in which they are prevented from rotating around the axis of rotation R.

According to another embodiment, the manipulating lever 41 operates alternately. In this case, while the manipulating lever 41 is being kept in the locked position, even when the manipulating force applied to the manipulating lever 41 is released, the manipulating lever 41 is kept in the locked position by the known actuating mechanism. The angularly movable member 33 and the shaft 3 are kept in the engaged position, keeping the end effector 5 and the shaft 3 prevented from rotating around the axis of rotation R.

While the manipulating lever 41 is being positioned in the locked position and the manipulating lever 41 is being released from the manipulating force, when the index finger F2 or the middle finger F3 applies a manipulating force to the manipulating lever 41 toward the proximal-end side, the manipulating lever 41 is moved to the unlocked position. As the manipulating lever 41 is moved from the locked position to the unlocked position, the angularly movable member 33 and the shaft 3 switch from the engaged position to the disengaged position. Therefore, the end effector 5 and the shaft 3 are released from the position in which they are prevented from rotating around the axis of rotation R.

According to the present embodiment, both when a manipulation is made to prevent the end effector 5 and the shaft 3 from rotating and when a manipulation is made to release the end effector 5 and the shaft 3 from the position in which they are prevented from rotating, a manipulating force directed toward the proximal-end side is applied from the index finger F2 or the middle finger F3 to the manipulating lever 41. Therefore, in both a manipulation to prevent the end effector 5 and the shaft 5 from rotating, i.e., a manipulation to move the manipulating lever 41 to the locked position, and a manipulation to release the end effector 5 and the shaft 3 from the position in which they are prevented from rotating, i.e., a manipulation to move the manipulating lever 41 to the unlocked position, it is easy to apply a manipulating force to the manipulating lever 41.

According to the present embodiment, the outer circumferential surface of the engaging portion 31 is of a serrated shape or gear shape. However, the engaging portion 31 is not limited to such a structure. The engaging portion may be in the form of a disk whose outer circumferential surface is made of a frictional material, for example. In such a case, when the manipulating lever 41 is in the locked position, the protruding portion 37 is held in abutment against the outer circumferential surface of the engaging portion 31. When the protruding portion 37 and the outer circumferential surface of the engaging portion 31 abut against each other, a frictional force is developed between the protruding portion 37 and the outer circumferential surface of the engaging portion 31. The frictional force developed between the protruding portion 37 and the outer circumferential surface of the engaging portion 31 prevents the engaging portion 31 from rotating in unison with the shaft 3 around the axis of rotation R with respect to the housing 2. In other words, the angularly movable member or locking member 33 may be of any structure for restraining or preventing the rotation of the shaft 3 around the axis of rotation R by engaging the shaft 3 or the engaging portion 31.

First Modification of the First Embodiment

According to the present embodiment, the rotary member 25 is disposed on the shaft 3 at the distal-end side of the housing 2. However, the rotary member 25 is not limited to such a layout. According to a first modification of the first embodiment illustrated in FIG. 5, the rotary member 25 may be mounted on the shaft 3 within the housing 2. In this case, the rotary member 25 is disposed in the housing body 11 more closely to the proximal-end side, e.g., the proximal-end portion of the housing body 11, than to the distal end of the housing body 11, i.e., the distal end of the housing 2. The rotary member 25 rotates in unison with the shaft 3 around the axis of rotation R. The housing body 11 has an opening 14 defined in an outer surface thereof around the axis of rotation R, i.e., the longitudinal axis C. The rotary member 25 is exposed outwardly from the outer surface of the housing body 11 through the opening 14.

According to the present modification, while the housing 2 of the treatment tool 1 is being held by one hand H0, the thumb F1 operates the rotary member 25 to adjust the angular position of the end effector 5 around the axis of rotation R. According to the present modification, therefore, as with the first embodiment, a manipulating force for moving the manipulating lever 41 is applied from the index finger F2 or the middle finger F3 to the manipulating lever 41. According to the present modification, consequently, as with the first embodiment, even if an angular moment is produced around the axis of rotation R by a force acting on the end effector 5, the end effector 5 and the shaft 3 are effectively prevented from rotating around the axis of rotation R.

Second Modification of the First Embodiment

Figure 6:
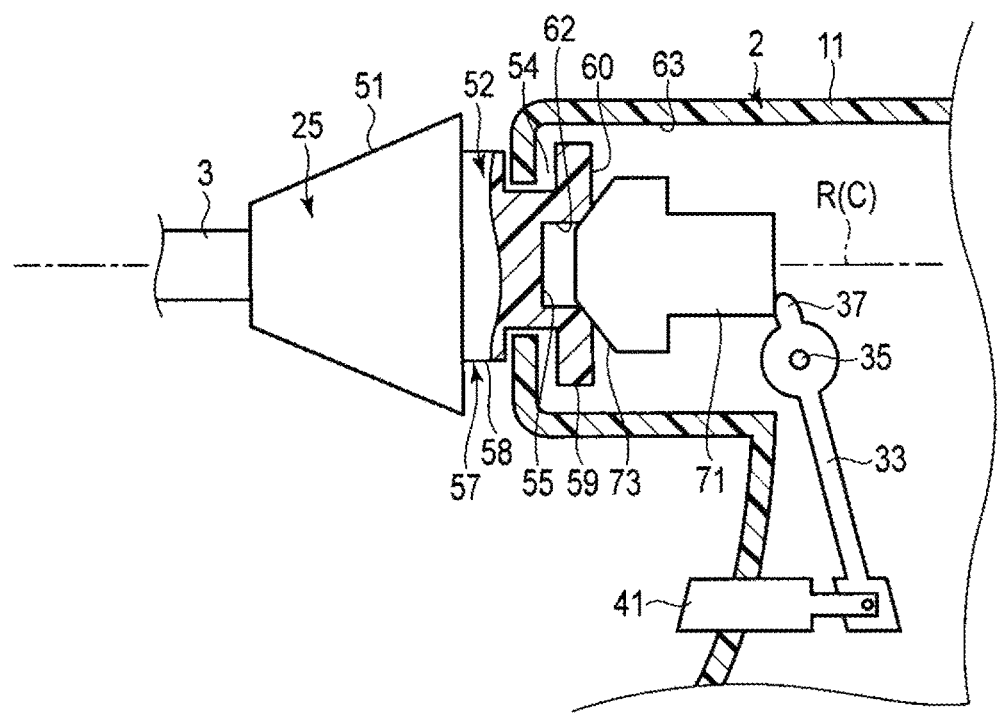
FIG. 6 is a schematic view of a locking member and a manipulating member that are disposed in a housing according to a second modification of the first embodiment, illustrated in a cross section substantially perpendicular to the widthwise directions of the housing.

FIG. 6 is a view illustrating the rotary member 25 and the inside of the housing body 11 according to a second modification of the first embodiment. As illustrated in FIG. 6, the rotary member 25 includes a manipulating portion 51 and a joint member 52 disposed on a proximal-end side of the manipulating portion 51. The joint member 52 is made of an elastic material. The joint member 52 has an outer circumferential surface 57. The outer circumferential surface 57 has an engaging groove 54 defined therein around the axis of rotation R. The engaging groove 54 is recessed from the outer circumferential surface 57 toward the axis of rotation R. The outer circumferential surface 57 includes a distal-end-side outer circumferential surface 58 extending on a distal-end side of the engaging groove 54 and a proximal-end-side outer circumferential surface 59 extending on a proximal-end side of the engaging groove 54. The housing body 11 has an outer casing whose distal end engages in the engaging groove 54 around the axis of rotation R. Therefore, the rotary member 25 and the shaft 3 are prevented from moving in the directions along the axis of rotation R with respect to the housing 2. The proximal-end-side outer circumferential surface 59 is positioned within the housing body 11.

Figure 7:
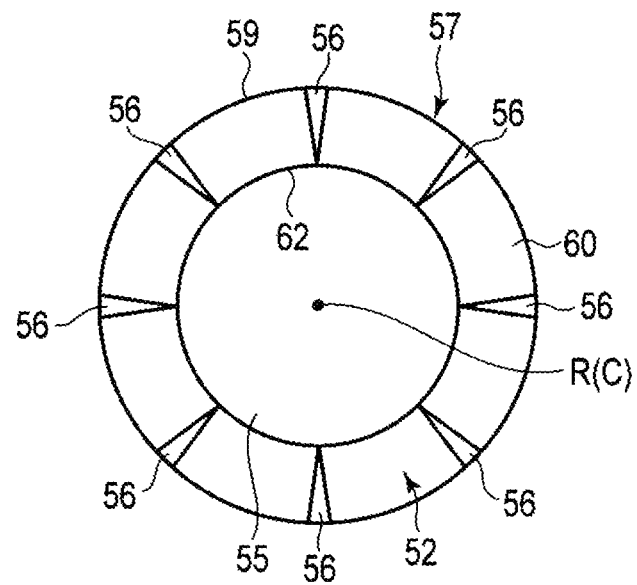
FIG. 7 is a schematic view of a rotary member according to the second modification of the first embodiment, as viewed from a proximal-end side thereof.

FIG. 7 is a view of the joint member 52 as viewed from a proximal-end side thereof. As illustrated in FIGS. 6 and 7, the joint member 52 includes a proximal-end face 60 facing the proximal-end side. The proximal-end face 60 has a cavity 55 defined therein that is recessed from the proximal-end face 60 toward a distal-end side thereof. The cavity 55 is of a circular shape around the axis of rotation R in a cross section that is transverse or substantially perpendicular to the axis of rotation R. The cavity 55 has an edge 62. The proximal-end-side outer circumferential surface 59 has a plurality of slots 56 defined therein that are spaced around the axis of rotation R. Each of the slots 56 extends from the proximal-end-side outer circumferential surface 59 toward the axis of rotation R up to the edge 62.

According to the present modification, in place of the engaging portion 31, a sliding member or locking member 71 is disposed within the housing body 11. The sliding member 71 extends along the axis of rotation R. The sliding member 71 is movable along the axis of rotation R or the longitudinal axis C with respect to the shaft 3. The sliding member 71 includes a distal-end portion whose diameter is gradually smaller toward a distal-end side thereof in a cross section transverse to the axis of rotation R. Consequently, the distal-end portion of the sliding member 71 has on its outer circumferential surface a slanted surface 73 that is slanted toward the axis of rotation R in a direction toward the distal-end side.

Figure 8:
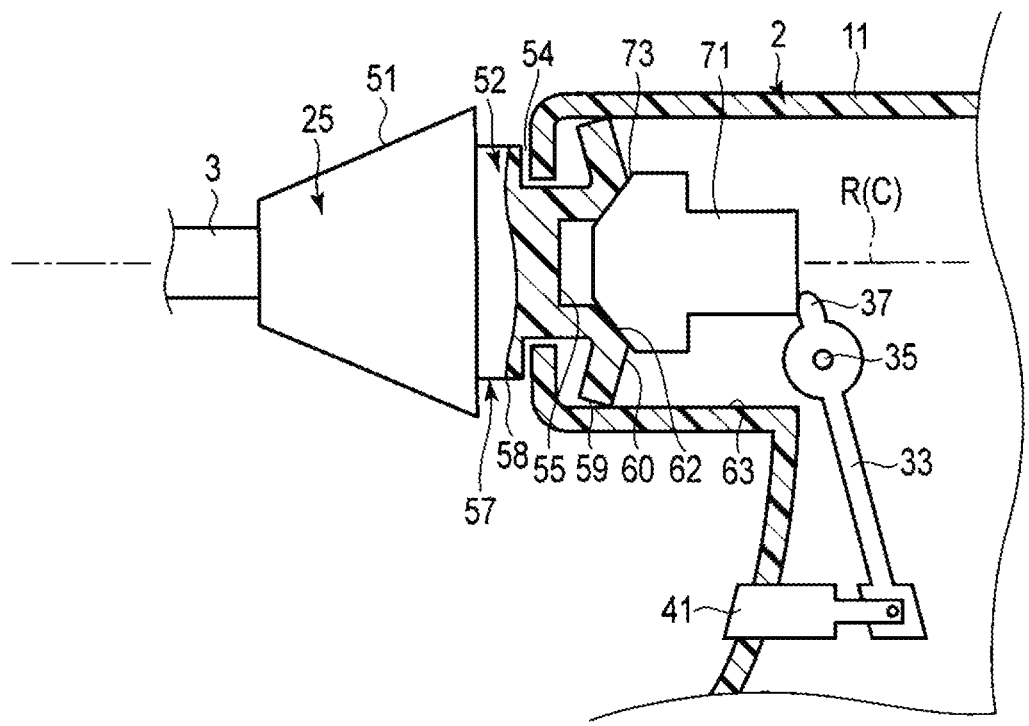
FIG. 8 is a schematic view of the locking member engaging the rotary member according to the second modification of the first embodiment, illustrated in a cross section substantially perpendicular to the widthwise directions of the housing.

FIG. 8 is a view illustrating the rotary member 25 and the inside of the housing body 11 at the time the manipulating lever or manipulating member 41 has moved to the locked position toward the proximal-end side. As depicted in FIG. 6, when the manipulating member 41 is positioned in the unlocked position, the protruding portion 37 of the angularly movable member 33 is held against the proximal end of the sliding member 71 and the slanted surface 73 of the sliding member 71 is held against the edge 62 of the rotary member 25. As illustrated in FIG. 8, according to the present modification, as with the first embodiment, when the manipulating lever 41 is moved toward the proximal-end side with respect to the housing 2, the angularly movable member 33 is angularly moved, moving the protruding portion 37 toward the distal-end side. According to the present modification, when the protruding portion 37 is moved toward the distal-end side, the sliding member 71 is pressed toward the distal-end side by the protruding portion 37. At this time, the edge 62 is pressed outwardly from the axis of rotation R and toward the distal-end side by the slanted surface 73. The space in each of the slots 56 is thus opened outwardly from the axis of rotation R, and the edge 62 is spread outwardly from the axis of rotation R. At the same time, the sliding member 71 is moved toward the distal-end side with respect to the joint member 52. At the proximal-end face 60 of the joint member 52, the edge 62 is spread outwardly from the axis of rotation R, so that the proximal-end-side outer circumferential surface 59 is spread outwardly from the axis of rotation R until the proximal-end-side outer circumferential surface 59 abuts against an inner surface 63 of the housing body 11. When the shaft 3 is rotated around the axis of rotation R with respect to the housing 2, a frictional force is developed between the proximal-end-side outer circumferential surface 59 of the rotary member 25 and the inner surface 63 of the housing body 11. The frictional force developed between the proximal-end-side outer circumferential surface 59 and the inner surface 63 prevents the rotary member 25 from rotating in unison with the shaft 3 around the axis of rotation R with respect to the housing 2.

According to the present embodiment, the sliding member 71 is used as a locking member for restraining or preventing the rotation of the shaft 3 around the axis of rotation R with respect to the housing 2 when the sliding member 71 engages the shaft 3 or the rotary member 25. When the sliding member 71 has its distal end engaging in the cavity 55 in the rotary member 25, the locking member or sliding member 71 and the shaft 3 engage each other in an engaged position. When the sliding member 71 has its distal end not engaging in the cavity 55 in the rotary member 25, the locking member or sliding member 71 and the shaft 3 disengage each other in a disengaged position. According to the present modification, when the manipulating lever or manipulating member 41 is moved from an unlocked position to a locked position, the locking member or sliding member 71 and the shaft 3 switch from the disengaged position to the engaged position, preventing the shaft 3 from rotating around the axis of rotation R with respect to the housing 2. According to the present modification, consequently, as with the first embodiment, even if an angular moment is produced around the axis of rotation R by a force acting on the end effector 5, when the manipulating lever 41 as a manipulating member is moved in directions or first directions along the axis of rotation R, the end effector 5 and the shaft 3 are effectively prevented from rotating around the axis of rotation R. In other words, the manipulating lever 41 is a manipulating member movable between a locked position in which the locking member or the sliding member 71 and the shaft 3 engage each other and an unlocked position in which the locking member or the sliding member 71 and the shaft 3 disengage each other.

Second Embodiment

Figure 10:
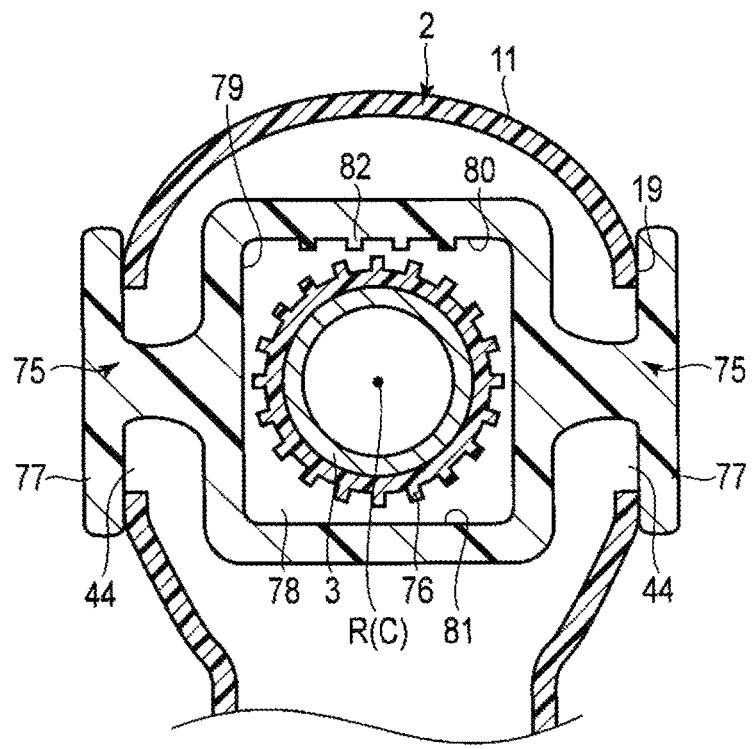
FIG. 10 is a cross-sectional view taken along line A-A of FIG. 9.
Figure 11:
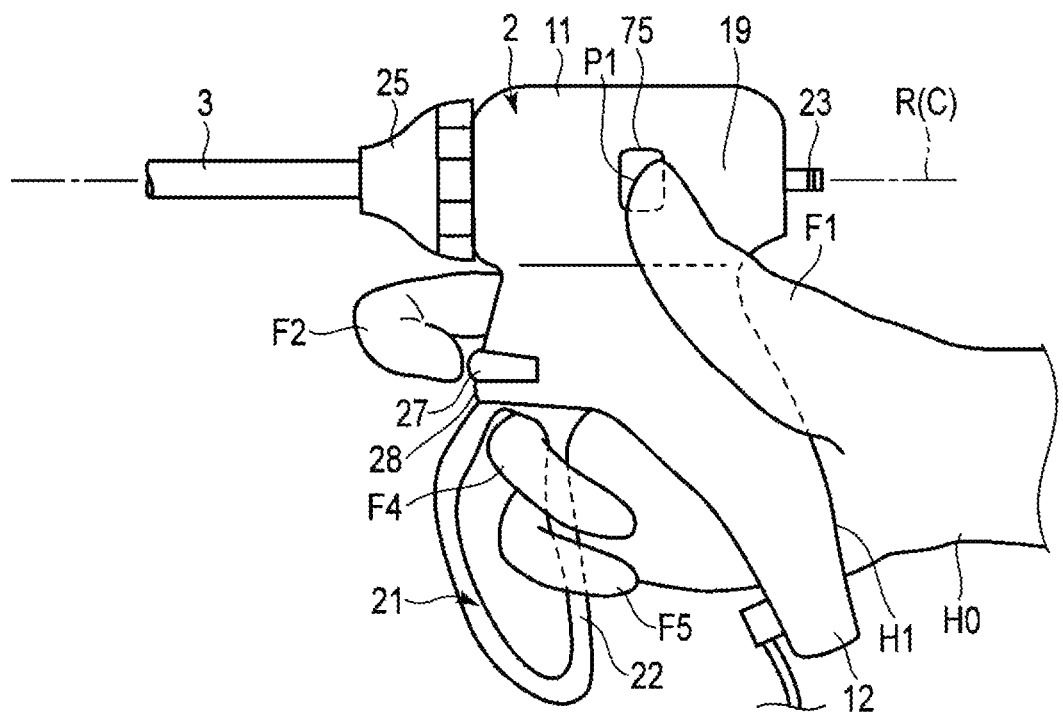
FIG. 11 is a schematic view of the housing according to the second embodiment that is held by a hand, as viewed from one side of the housing in its widthwise directions.

Next, a second embodiment of the present disclosure will be described hereinafter with reference to FIGS. 9 through 11. The second embodiment is based on the first embodiment that is modified as described hereinafter. Those part of the second embodiment which are identical to those of the first embodiment are denoted by identical reference characters, and will not be described in detail below.

Figure 9:
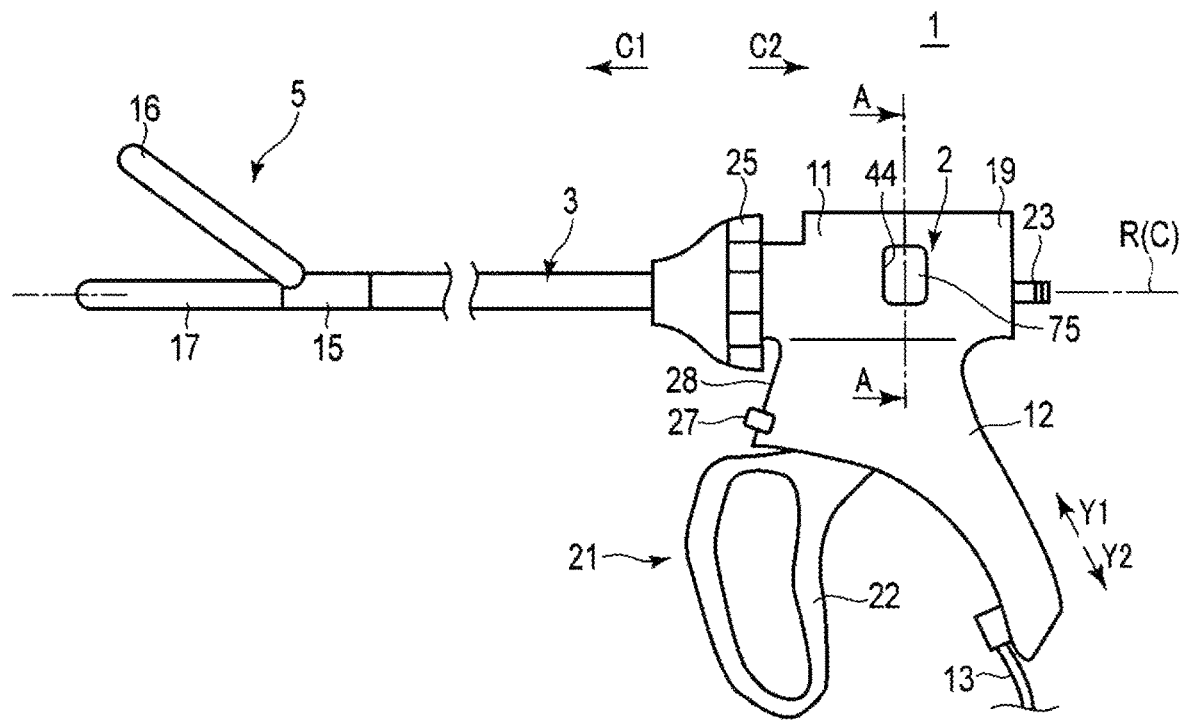
FIG. 9 is a schematic view of a treatment tool according to a second embodiment, as viewed from one side of a housing thereof in its widthwise directions.

FIG. 9 is a view of a treatment tool 1 according to the present embodiment. FIG. 10 is a cross-sectional view taken along line A-A of FIG. 9. As illustrated in FIGS. 9 and 10, a housing body 11 has on an outer surface thereof side faces 19 that fade in the widthwise directions of a housing 2. As illustrated in FIG. 10, the side faces 19 have respective openings 44 defined therein. The openings 44 are through holes extending through the outer surface of the housing body 11 in the widthwise directions.

A sheath or shaft 3 that is inserted into the housing 2 from a distal-end side thereof extends along an axis of rotation R in a housing body 11. The shaft 3 has on an outer surface thereof an engaging portion 76 extending around the axis of rotation R. The engaging portion 76 has a serrated shape, for example. A slide member or locking member 75 extends in the widthwise directions in the housing body 11. The slide member 75 has both end portions in the widthwise directions that project respectively through the openings 44 defined in the housing body 11 out of the housing body 11. The end portions of the slide member 75 that project out of the housing body 11 is used as slide manipulators or manipulating members 77. The slide member 75 is movable in direction or third direction transverse to the axis of rotation R and along the side faces 19.

The slide member 75 has a hole 78 defined therein in a cross section taken along line A-A transverse to the axis of rotation R, with the shaft 3 inserted through the hole 78. The hole 78 is a through hole extending through the slide member 75 along the axis of rotation R. The shaft 3 is inserted in the hole 78 along the axis of rotation R. The hole 78 is defined by confronting faces 79 of the slide member 75 that confront an outer circumferential surface of the shaft 3. The confronting faces 79 include, in directions transverse or substantially perpendicular to the axis of rotation R and the widthwise directions, a first confronting face 80 that faces a side where the grip 12 is disposed with respect to the axis of rotation R and a second confronting face 81 that faces opposite the first confronting face 80. The first confronting face 80 has an engaging portion 82 for engaging the engaging portion 76 of the shaft 3. The engaging portion 82 is of a serrated shape, for example.

When the slide member 75 moves in the directions or third directions in which the grip 12 extends, the engaging portion 82 of the first confronting face 80 moves in the directions transverse or substantially perpendicular to the axis of rotation R and the widthwise directions. When the engaging portion 82 moves in the directions transverse or substantially perpendicular to the axis of rotation R and the widthwise directions, it moves between a position in which the engaging portion 82 engages the engaging portion 76 of the shaft 3 and a position in which the engaging portion 82 does not engage the engaging portion 76 of the shaft 3. In other words, when the slide member 75 or the slide manipulators 77 move in the directions or third directions transverse to the axis of rotation R and along the side faces 19, it switches between a disengaged position in which the engaging portion 76 of the shaft 3 and the engaging portion 82 of the slide member 75 disengage each other and an engaged position in which the engaging portion 76 of the shaft 3 and the engaging portion 82 of the slide member 75 engage each other. When the engaging portion 76 of the shaft 3 and the engaging portion 82 of the slide member 75 engage each other, the shaft 3 is prevented from rotating around the axis of rotation R with respect to the housing 2. In other words, the slide manipulators 77 are manipulating members movable between an unlocked position in which the shaft 3 and the locking member or slide member 75 disengage with each other and a locked position in which the shaft 3 and the locking member or slide member 75 engage with each other, when the slide manipulators 77 move in the directions or third directions transverse to the axis of rotation R and along the side face 19.

Next, operation and advantages of the treatment tool 1 according to the present embodiment will be described below. FIG. 11 is a view illustrating the housing 2 of the treatment tool 1 according to the present embodiment that is held by a hand H0, i.e., the right hand in FIG. 11. FIG. 11 is viewed from one side or the arrow W1 side in the widthwise directions of the housing 2. As illustrated in FIG. 11, as with the first embodiment, the operator holds the housing 2 of the treatment tool 1 according to the present embodiment with one hand thereof, i.e., the right hand in FIG. 11, and treats a treatment target such as a living tissue or the like using the treatment tool 1.

When an angular moment is produced around the axis of rotation R by the force acting on the end effector 5, the operator brings the thumb F1 that extends from the grip 12 to one of the side faces 19 into abutment against the slide manipulator 77. The operator then presses, with the thumb F1, the slide manipulator 77 in one of the directions or third directions transverse to the axis of rotation R and along the side face 19 toward the grip 12. Now, a manipulating force is applied to the slide manipulator 77, moving the slide member 75 from the unlocked position to the locked position. When the slide member 75 is moved from the unlocked position to the locked position, the engaging portion 76 of the shaft 3 and the engaging portion 82 of the slide member 75 switch from the disengaged position to the engaged position. In other words, the slide member 75 and the shaft 3 switch from the disengaged position to the engaged position. As the slide member 75 and the shaft 3 switch from the disengaged position to the engaged position, the end effector 5 and the shaft 3 are prevented from rotating around the axis of rotation R, as described hereinbefore. In other words, the slide manipulators 77 are manipulating members for causing the slide member 75 and the shaft 3 to switch between the engaged position and the disengaged position when they move in the directions or third directions transverse to the axis of rotation and along the side faces 19.

According to the present embodiment, even if an angular moment is produced around the axis of rotation R by a force acting on the end effector 5, the locking member or the slide member 75 engages the shaft 3 by applying a manipulating force from the thumb F1 to the manipulating members or the slide manipulators 77. As a result, the end effector 5 and the shaft 3 are effectively prevented from rotating around the axis of rotation R. The performance of a treatment that is performed while the treatment target is gripped between the gripping members 16, 17 is thus adequately maintained.

With a pistol-shaped treatment tool such as the treatment tool 1, while the housing 2 is being held by the hand H0, e.g., the right hand, the thumb F1 extends from the palm H1 onto one of the side faces 19 of the housing 2 toward the distal-end side. According to the present embodiment, the slide manipulators 77 are disposed on the side faces 19 of the housing 2. Therefore, while the housing 2 is being held by the hand H0, the slide manipulators or manipulating members 77 are positioned in a range where the thumb F1 can abut against one of the slide manipulators 77. According to the present embodiment, therefore, the operator can operate the slide manipulators 77 using only one hand H0 to prevent the end effector 5 and the shaft 3 from rotating around the axis of rotation R.

For applying a manipulating force to the slide manipulators 77 disposed on the side faces 19 of the housing 2, the pad P1 of the thumb F1 extending onto the side face 19 is held against the slide manipulator 77. Therefore, it is easy for the thumb F1 to apply a manipulating force to the slide manipulator 77 in a direction along the side face 19. According to the present embodiment, when the slide member 75 moves to a side where the grip 12 is positioned with respect to the axis of rotation R along the direction in which the grip 12 extends, the slide member 75 or the locking member and the shaft 3 switch from the disengaged position to the engaged position. In other words, when the slide member 75 moves in a direction along the side faces 19, the slide member 75 or the locking member and the shaft 3 switch from the disengaged position to the engaged position. According to the present embodiment, therefore, it is easy for the thumb F1 to apply a manipulating force tending to move the slide manipulators 77 to the locked position to the slide manipulators 77. The operator can thus operate the slide manipulators 77 with one hand and with ease. Consequently, the end effector 5 and the shaft 3 are effectively prevented from rotating around the axis of rotation R.

According to the present embodiment, when the slide member 75 moves to the side where the grip 12 is positioned with respect to the axis of rotation R along the direction in which the grip 12 extends, the position in which the shaft 3 and the locking member or the slide member 75 disengage each other, i.e., the disengaged position, switches to the position in which the shaft 3 and the locking member or the slide member 75 engage each other, i.e., the engaged position. However, the shaft 3 and the locking member or the slide member 75 are not limited to such an arrangement. According to an embodiment, when the slide member 75 moves to the side where the grip 12 is positioned with respect to the axis of rotation R along the direction in which the grip 12 extends, the position in which the shaft 3 and the locking member or the slide member 75 engage each other, i.e., the engaged position, switches to the position in which the shaft 3 and the locking member or the slide member 75 disengage each other, i.e., the disengaged position. In this case, the engaging portion 82 is disposed on the second confronting face 81 of the slide member 75. When the thumb F1 applies a manipulating force to move the slide member 75 to a side that is opposite the side where the grip 12 is positioned with respect to the axis of rotation R in the direction in which the grip 12 extends, the engaging portion 82 of the slide member 75 engages the engaging portion 76 of the shaft 3, causing the engaging portion 76 of the shaft 3 and the engaging portion 82 of the slide member 75 to switch to the engaged position. In this case, too, the disengaged position switches to the engaged position by moving the slide member 75 in the direction along the side face 19. Therefore, it is easy to apply a manipulating force tending to move the slide manipulator 77 to the locked position from the thumb F1 to the slide manipulator 77.

The slide member 75 may be movable in directions along the axis of rotation R with respect to the housing 2. In this case, when the slide member 75 is moved in a direction or first direction along the axis of rotation R with respect to the housing 2, the sliding members 75 or the locking members and the shaft 3 switch between the disengaged position and the engaged position. In this case, too, the disengaged position switches to the engaged position by moving the slide member 75 in the direction along the side face 19. Therefore, it is easy to apply a manipulating force tending to move the slide manipulator 77 to the locked position from the thumb F1 to the slide manipulator 77.

First Modification of the Second Embodiment

Figure 12:
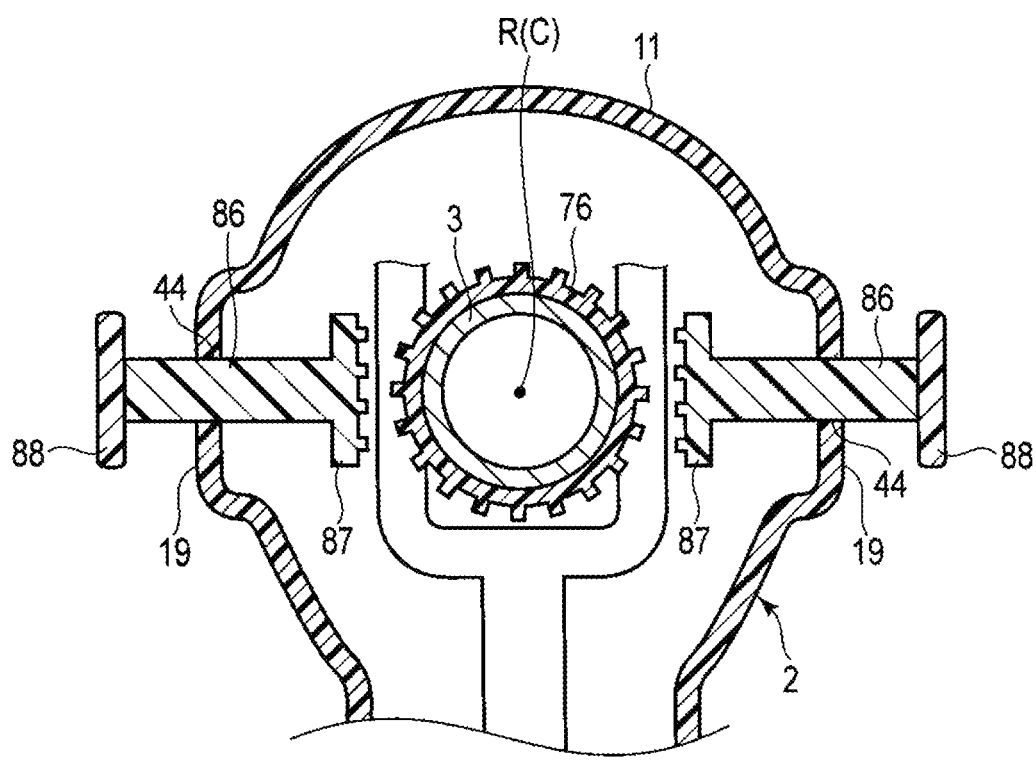
FIG. 12 is a cross-sectional view taken along line A-A of FIG. 9, illustrating a first modification of the second embodiment.

FIG. 12 is a cross-sectional view taken along line A-A of FIG. 9, illustrating a first modification of the second embodiment. According to the present modification, as illustrated in FIG. 12, rod-shaped members 86 or locking members are used instead of the slide member 75. Each of the rod-shaped members 86 extends in widthwise directions, and is fitted in an opening 44 defined in one of the side faces 19. The rod-shaped member 86 has an engaging portion 87 for engaging the engaging portion 76 of the shaft 3. The engaging portion 87 is disposed on an end of the rod-shaped member 86 that is positioned in the housing body 11. The engaging portion 87 has a serrated shape, for example. The rod-shaped member 86 also has a pressing member 88 or a manipulating member. The pressing member 88 is disposed on an end of the rod-shaped member 86 extending through the opening 44, which end is positioned outside of the housing body 11.

According to the present modification, when an angular moment is produced around the axis of rotation R by the force acting on the end effector 5, the operator brings the thumb F1 that extends from the grip 12 onto one of the side faces 19 into abutment against the pressing member 88 of the rod-shaped member 86. The operator then presses, with the thumb F1, the pressing member 88 widthwise in a direction toward the axis of rotation R, i.e., in a second direction. A manipulating force is thus applied to the pressing member 88, moving the rod-shaped member 86 from an unlocked position to a locked position. When the rod-shaped member 86 is moved from the unlocked position to the locked position, the engaging portion 76 of the shaft 3 and the engaging portion 87 of the rod-shaped member 86 switch from a disengaged position to an engaged position, as described hereinbefore. As the rod-shaped member 86 and the shaft 3 switch from the disengaged position to the engaged position, the end effector 5 and the shaft 3 are prevented from rotating around the axis of rotation R, as described hereinbefore. In other words, the pressing members 88 is used as manipulating members that are movable between the locked position in which the locking member or the rod-shaped member 86 and the shaft 3 engage each other and the unlocked position in which the locking member or the rod-shaped member 86 and the shaft 3 disengage each other, when the pressing members 88 move in the direction toward the axis of rotation R, i.e., the second direction, with respect to the housing 2.

According to the present modification, too, even if an angular moment is produced around the axis of rotation R by a force acting on the end effector 5, the locking member or the rod-shaped member 86 engages the shaft 3 due to a force applied from the thumb F1 to the manipulating member or the pressing member 88. The end effector 5 and the shaft 3 are effectively prevented from rotating around the axis of rotation R. The performance of a treatment that is performed while the treatment target is gripped between the gripping members 16, 17 is thus adequately maintained.

With a pistol-shaped treatment tool such as the treatment tool 1, while the housing 2 is being held by one hand H0, e.g., the right hand, the thumb F1 extends from the palm H1 onto one of the side faces 19 of the housing 2 toward the distal-end side. According to the present modification, the manipulating member or the pressing member 88 is disposed in a range where the thumb F1 can abut against the pressing member 88. According to the present embodiment, therefore, the operator can operate the manipulating member or the pressing member 88 using only one hand H0 to prevent the end effector 5 and the shaft 3 from rotating around the axis of rotation R.

For applying a manipulating force to the pressing member 88 disposed on one of the side faces 19 of the housing 2, the pad P1 of the thumb F1 extending onto the side face 19 is held against the pressing member 88. Therefore, it is easy for the thumb F1 to apply a manipulating force to the pressing member 88 in a direction toward the axis of rotation R. According to the present modification, when the locking member or the rod-shaped member 86 moves in the direction toward the axis of rotation R, i.e., the second direction with respect to the housing 2, the locking member or the rod-shaped member 86 and the shaft 3 switch from the disengaged position to the engaged position. According to the present embodiment, therefore, it is easy for the thumb F1 to apply a manipulating force tending to move the rod-shaped member 86 to the locked position to the manipulating member or the pressing member 88. The operator can thus operate the manipulating member or the pressing member 88 with one hand and with ease. Consequently, the end effector 5 and the shaft 3 are effectively prevented from rotating around the axis of rotation R.

Third Embodiment

Figure 14:
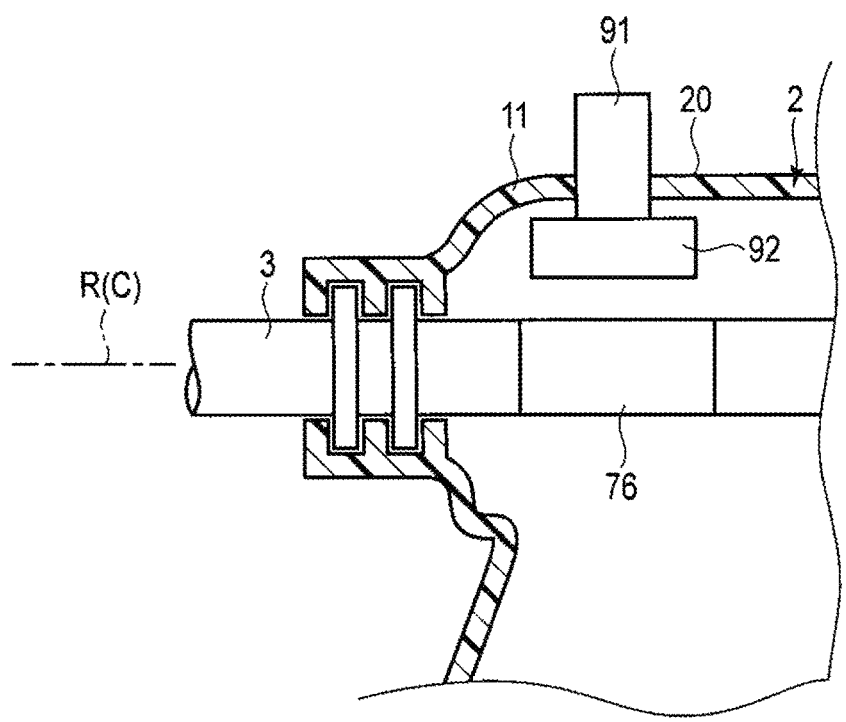
FIG. 14 is a schematic view of a locking member and a manipulating member according to the third embodiment, illustrated in a cross section substantially perpendicular to the widthwise directions of the housing.
Figure 15:
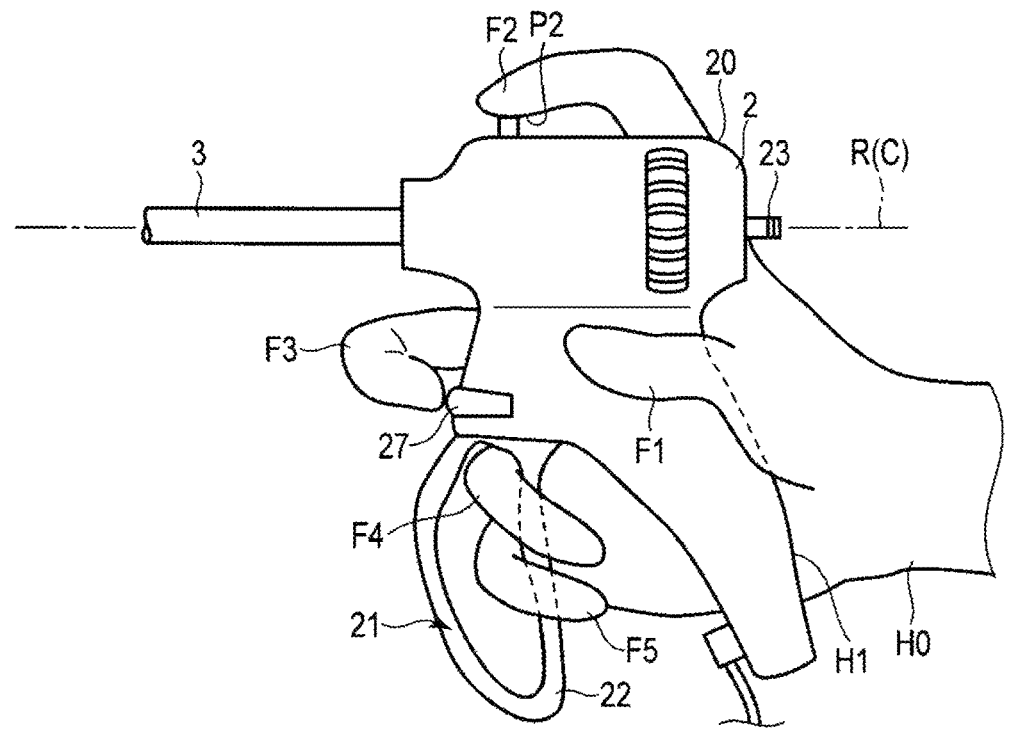
FIG. 15 is a schematic view of the housing according to the third embodiment that is held by a hand, as viewed from one side of the housing in its widthwise directions.

Next, a third embodiment of the present disclosure will be described hereinafter with reference to FIGS. 13 through 15. The third embodiment is based on the first embodiment that is modified as described hereinafter. Those part of the third embodiment which are identical to those of the first embodiment are denoted by identical reference characters, and will not be described in detail below.

Figure 13:
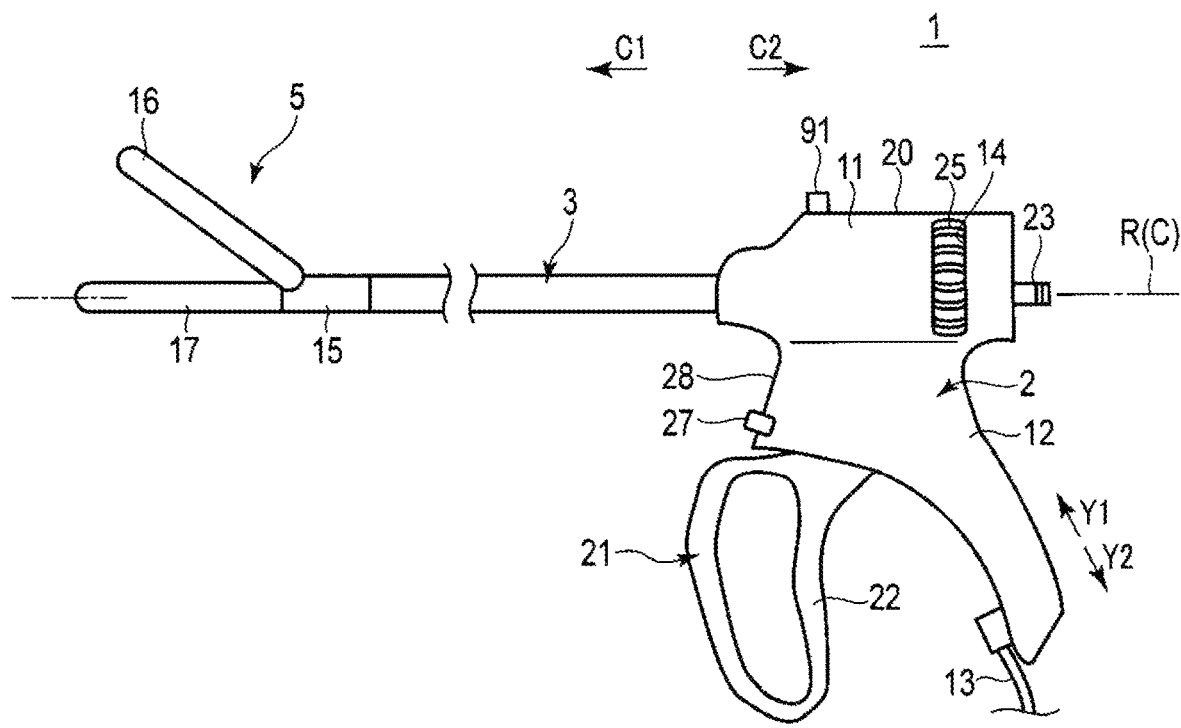
FIG. 13 is a schematic view of a treatment tool according to a third embodiment, as viewed from one side of a housing thereof in its widthwise directions.

FIG. 13 is a view of a treatment tool 1 according to the present embodiment. FIG. 14 is a view depicting the inside of a housing body 11 according to the present embodiment. As illustrated in FIGS. 13 and 14, according to the present embodiment, as with the first modification of the first embodiment, a rotary member 25 is disposed on a shaft 3 in the housing 2. The rotary member 25 is exposed out of the housing body 11 through an opening 14 that is defined in an outer surface of the housing body 11. The housing body 11 has an upper face 20 that faces away from the side where a grip 12 is positioned with respect to the axis of rotation R. A switch 91 or a manipulating member is disposed on the upper face 20. The switch 91 extends through the upper face 20 and is movable in directions transverse or substantially perpendicular to the upper face 20 with respect to the housing 2. In other words, the switch 91 is movable in a direction toward the axis of rotation R, i.e., a second direction. The switch 91 is disposed on a distal-end side of the housing body 11.

The switch 91 has an end portion extending into the housing body 11 in a direction transverse or substantially perpendicular to the upper face 20. An abutting member 92 or a locking member is disposed on the end portion of the switch 91. The abutting member 92 is made of a frictional material, for example. The abutting member 92 is movable in unison with the switch 91 in directions transverse to the upper face 20 with respect to the housing 2. According to the present embodiment, as with the second embodiment, etc., an engaging portion 76 is disposed on an outer surface of the shaft 3. The engaging portion 76 is made of a frictional material, for example. When the switch 91 and the abutting member 92 move in directions transverse or substantially perpendicular to the upper face 20, the abutting member 92 moves between a position in which the abutting member 92 engages the engaging portion 76 on the shaft 3 and a position in which the abutting member 92 disengages the engaging portion 76 on the shaft 3. In other words, when the switch 91 moves directions transverse or substantially perpendicular to the upper face 20, the abutting member 92 and the engaging portion 76 on the shaft 3 switch between an engaged position and a disengaged position. In other words, the switch 91 is a manipulating member movable between a locked position in which the locking member or the abutting member 92 and the shaft 3 engage each other and an unlocked position in which the locking member or the abutting member 92 and the shaft 3 disengage each other.

Next, operation and advantages of the treatment tool 1 according to the present embodiment will be described below. FIG. 15 is a view illustrating the housing 2 of the treatment tool 1 according to the present embodiment that is held by a hand H0, i.e., the right hand in FIG. 15. FIG. 15 is viewed from one side or the arrow W1 side in the widthwise directions of the housing 2. As illustrated in FIG. 15, as with the first embodiment, etc., the operator holds the housing 2 of the treatment tool 1 according to the present embodiment with one hand thereof, i.e., the right hand in FIG. 15, and treats a treatment target such as a living tissue or the like using the treatment tool 1.

When an angular moment is produced around the axis of rotation R by a force acting on the end effector 5, the operator brings the index finger F2 that extends from the grip 12 over the upper face 20 into abutment against the switch 91. The operator then presses, with the index finger F2, the switch 91 in a direction toward the axis of rotation R along the directions in which the grip 12 extends. A manipulating force is now applied to the switch 91, moving the switch 91 from the unlocked position to the locked position. When the switch 91 is moved from the unlocked position to the locked position, the engaging portion 76 on the shaft 3 and the abutting member 92 switch from the disengaged position to the engaged position. In other words, the locking member or the abutting member 92 and the shaft 3 switch from the disengaged position to the engaged position. As the locking member or the abutting member 92 and the shaft 3 switch from the disengaged position to the engaged position, the end effector 5 and the shaft 3 are prevented from rotating around the axis of rotation R, as described hereinbefore.

According to the present embodiment, even if an angular moment is produced around the axis of rotation R by a force acting on the end effector 5, the locking member or the abutting member 92 engages the shaft 3 by applying a manipulating force from the index finger F2 to the switch 92 as the manipulating member. As a result, the end effector 5 and the shaft 3 are effectively prevented from rotating around the axis of rotation R. The performance of a treatment that is performed while the treatment target is gripped between the gripping members 16, 17 is thus adequately maintained.

With a pistol-shaped treatment tool such as the treatment tool 1, while the housing 2 is being held by the hand H0, e.g., the right hand, the index finger F2 extends from the palm H1 onto the upper face 20 of the housing body 11. According to the present embodiment, the switch 91 is disposed on the upper face 20 of the housing 2. Therefore, while the housing 2 is being held by the hand H0, the manipulating member or the switch 91 is positioned in a range where the index finger F2 can abut against the switch 91. According to the present embodiment, therefore, the operator can operate the switch 91 using only one hand H0 to prevent the end effector 5 and the shaft 3 from rotating around the axis of rotation R.

For applying a manipulating force to the switch 91 disposed on the upper face 20 of the housing 2, the pad P2 of the index finger F2 extending onto the upper face 20 is held against the switch 20. Therefore, it is easy for the index finger F2 to apply a manipulating force to the switch 91 in a direction toward the axis of rotation R. According to the present embodiment, when the switch 91 moves in the direction toward the axis of rotation R, the locking member or the abutting member 92 and the shaft 3 switch from the disengaged position to the engaged position. According to the present embodiment, therefore, it is easy for the index finger F2 to apply a manipulating force tending to move the switch 91 to the locked position to the switch 91. The operator can thus operate the switch 91 or the manipulating member with one hand and with ease. Consequently, the end effector 5 and the shaft 3 are effectively prevented from rotating around the axis of rotation R.

Other Modifications

Each of the slide manipulators 77, the pressing member 88, and the switch 91 described as manipulating members in the second embodiment and the third embodiment, etc. may be of the momentary type or the alternate type, as described hereinbefore with respect to the first embodiment.

Figure 16:
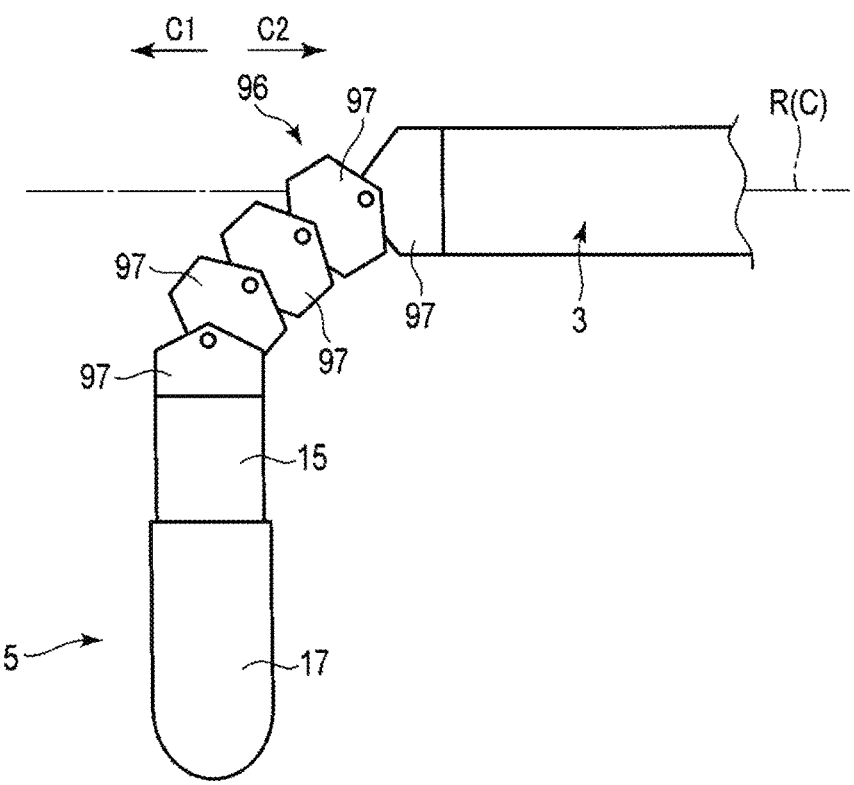
FIG. 16 is a schematic view illustrating the structure of a distal-end portion of a treatment tool according to a modification of the first through third embodiments.

The treatment tool in which an angular moment is produced around the axis R of rotation by a force acting on the end effector 5 is not limited to the treatment tool 1 with the bendable joint 18 according to the first embodiment or the like described hereinbefore. According to a modification of the first through third embodiments, as illustrated in FIG. 16, a bendable portion 96 may be disposed in place of the bendable joint 18 on the distal-end side of the shaft 3. The bendable portion 96 is made up of a plurality of arrayed bend elements 97 each angularly movably coupled to an adjacent bend element or elements 97 or a corresponding one or two of the bend elements 97. In place of the bending dial or bending manipulation input portion 23, a different bending manipulation input portion is disposed on the housing 2. The bendable portion 96 is actuated by operating this bending manipulation input portion. When the bendable portion 96 is actuated, the end effector 5 that includes the bendable portion 96 is bent with respect to the shaft 3 or the axis of rotation R. When a force acts on the end effector 5 that is being bent with respect to the shaft 3, since the force acts thereon at a position spaced from the axis of rotation R, as described hereinbefore, an angular moment may possibly be produced around the axis of rotation R or the central axis of the shaft 3. According to the present modification, since the treatment tool has the manipulating member 41; 77; 88; 91 and the locking member 33; 71; 75; 86; 92 that are similar to those of the embodiment, etc. described hereinbefore, even if an angular moment is produced around the axis of rotation R by the force acting on the end effector 5, the locking member 33; 71; 75; 86; 92 and the shaft 3 switch from the disengaged position to the engaged position. Consequently, the end effector 5 and the shaft 3 are effectively prevented from being rotated around the axis of rotation R.

Figure 17:
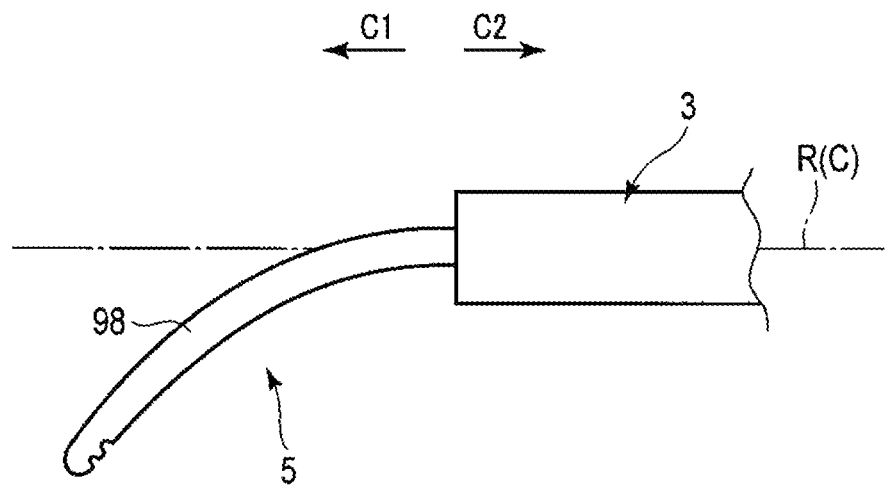
FIG. 17 is a schematic view illustrating the structure of a distal-end portion of a treatment tool according to another modification of the first through third embodiments.

According to another modification illustrated in FIG. 17, an end effector 5 projects toward the distal-end side from the distal end of the shaft 3. The end effector 5 includes a curved extension 98 extending so as to be capable to being curved with respect to the shaft 3 or the axis of rotation R. When a force acts on the end effector 5 at a region on the distal-end side from the curved extension 98, since the force acts thereon at a position spaced from the axis of rotation R, as described hereinbefore, an angular moment may possibly be produced around the axis of rotation R or the central axis of the shaft 3. According to the present modification, since the treatment tool has the manipulating member 41; 77; 88; 91 and the locking member 33; 71; 75; 86; 92 that are similar to those of the embodiment, etc. described hereinbefore, even if an angular moment is produced around the axis of rotation R by the force acting on the end effector 5, the locking member 33; 71; 75; 86; 92 and the shaft 3 switch from the disengaged position to the engaged position. Consequently, the end effector 5 and the shaft 3 are effectively prevented from being rotated around the axis of rotation R.

Figure 18:
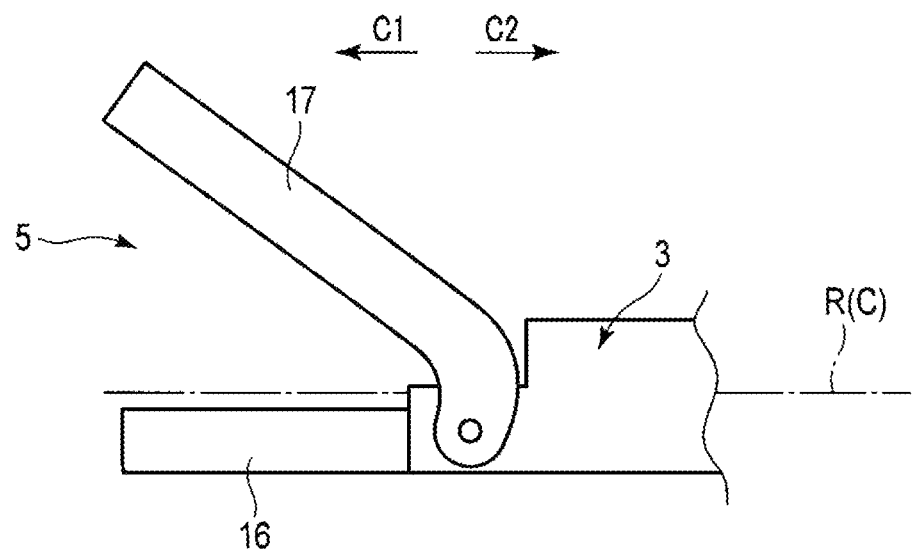
FIG. 18 is a schematic view illustrating the structure of a distal-end portion of a treatment tool according to still another modification of the first through third embodiments.

According to still another modification illustrated in FIG. 18, as with the first embodiment, a pair of gripping members 16, 17 are mounted on an end effector 5. According to the present modification, the treatment tool 1 is devoid of either of the bendable joint 18, the bendable portion 96, and the bendable extension 85. The treatment tool 1 with the gripping members 16, 17 may perform a treatment while the space between the gripping members 16, 17 is being open. While the space between the gripping members 16, 17 is being open, if a force acts on a gripping member, e.g., the second gripping member 17, angularly movably mounted on the shaft 3, since the force acts thereon at a position spaced from the axis of rotation R, as described hereinbefore, an angular moment may possibly be produced around the axis of rotation R or the central axis of the shaft 3. According to the present modification, since the treatment tool has the manipulating member 41; 77; 88; 91 and the locking member 33; 71; 75; 86; 92 that are similar to those of the embodiment, etc. described hereinbefore, even if an angular moment is produced around the axis of rotation R by the force acting on the end effector 5, the locking member 33; 71; 75; 86; 92 and the shaft 3 switch from the disengaged position to the engaged position. Consequently, the end effector 5 and the shaft 3 are effectively prevented from being rotated around the axis of rotation R.

According to the present embodiment, etc. described hereinbefore, the treatment tool 1 includes the housing 2 that can be held which has the side face 19 facing in a widthwise direction thereof, the shaft 3 that is rotatable around the predetermined axis of rotation R with respect to the housing 2, the end effector 5 disposed on a distal-end portion of the shaft 3 and rotatable in unison with the shaft 3 around the axis of rotation R, the locking member 33; 71; 75; 86; 92 disposed in the housing 2 so as to be engageable with the shaft 3 for restraining rotation of the shaft 3 around the axis of rotation R with respect to the housing 2 by engaging the shaft 3, and the manipulating member 41; 77; 88; 91 mounted on the housing 2 and movable with respect to the housing 2 in a first direction along the axis of rotation R, a second direction toward the axis of rotation, or a third direction along the side surface and transverse to the axis of rotation, for switching between the engaged position in which the locking member 33; 71; 75; 86; 92 and the shaft 3 engage each other and the disengaged position in which the locking member 33; 71; 75; 86; 92 and the shaft 3 disengage each other.

In sum, one aspect of the disclosed technology is directed to a treatment tool comprises a housing having a side surface facing in a widthwise direction thereof. An elongated member having respective proximal and distal ends. The elongated member is configured to be attached to the housing via the proximal end. The elongated member rotates around an axis of rotation with respect to the housing. An end effector is configured to be attached to the distal-end of the elongated member and rotates in unison with the elongated member around the axis of rotation. A locking member is configured to be attached to the housing so as to be engageable with the elongated member for restraining rotation of the elongated member around the axis of rotation with respect to the housing. A manipulating member is configured to be attached to the housing and being movable with respect to the housing in a first direction along the axis of rotation, a second direction toward the axis of rotation, or a third direction along the side surface and transverse to the axis of rotation, for switching from an engaged position to a disengaged position and vice versa. In the engaged position, the locking member and the elongated member engage with one another and in the disengaged position, the locking member and the elongated member disengage from one another.

The housing includes a grip extending downwardly in a direction transverse to the axis of rotation. The manipulating member is attached to the housing on a side where the grip is positioned with respect to the axis of rotation and more closely to a distal-end side of the treatment tool than the grip and is installed on an outer surface of the housing that faces the distal-end side and wherein the manipulating member moves in the first direction upon switching between the engaged position and the disengaged position. While the housing is being held by a hand, the palm and the thumb of the hand are held against the grip from the proximal-end side, and the manipulating member is positioned in a range where the index finger and/or the middle finger of the hand can abut against the manipulating member. The manipulating member causes the locking member and the elongated member to switch from the disengaged position to the engaged position by moving from a distal-end side to a proximal-end side in the first direction. The housing includes a grip attached thereto and extending downwardly in a direction transverse to the axis of rotation and the widthwise direction. The manipulating member is disposed on the side surface of the housing and moves in the first direction, the second direction, or the third direction upon switching between the engaged position and the disengaged position.

While the housing is being held by a hand, the palm and the thumb of the hand are held against the grip from the proximal-end side, and the manipulating member is positioned in a range where the thumb can abut against the manipulating member. The manipulating member causes the locking member and the elongated member to switch from the disengaged position to the engaged position by moving from a distal-end side of the treatment tool toward a proximal-end side of the treatment tool in the first direction, moving toward the axis of rotation in the second direction, or moving toward a side where the grip is positioned in the third direction. The housing includes a grip attached thereto and extending in a direction transverse to the axis of rotation. The manipulating member is disposed on the housing on a side of the axis of rotation that is opposite the grip and moves in the second direction upon switching between the engaged position and the disengaged position. While the housing is being held by a hand, the palm and the thumb of the hand are held against the grip from a proximal-end side of the treatment tool, and the manipulating member is positioned in a range where the index finger can abut against the manipulating member. The manipulating member causes the locking member and the elongated member to switch from the disengaged position to the engaged position by moving toward the axis of rotation in the second direction.

The manipulating member moves between a locked position in which the locking member and the elongated member engage with one another and an unlocked position in which the locking member and the elongated member disengage from one another. The manipulating member moves to the locked position by a first manipulating force that is applied thereto when the manipulating member is in the unlocked position. The manipulating member remains in the locked position even if the manipulating member is released from the manipulating force applied thereto when the manipulating member has been moved to the locked position by the first manipulating force. The manipulating member moves to the unlocked position by a second manipulating force applied thereto when the manipulating member is in the locked position. The manipulating member moves between a locked position in which the locking member and the elongated member engage with one another and in an unlocked position in which the locking member and the elongated member disengage from one another. The manipulating member moves to the locked position by a manipulating force that is applied thereto when the manipulating member is in the unlocked position. The manipulating member moves to the unlocked position by being released from the manipulating force applied thereto when the manipulating member has been moved to the locked position by the manipulating force.

The end effector is capable of being bended and/or curved with respect to the axis of rotation. The elongated member has a rotary member coupled to the housing from the distal-end, exposed outwardly of the housing, and rotates in unison with the elongated member around the axis of rotation. The elongated member is inserted into the housing and the elongated member includes a rotary member disposed more closely to a proximal-end side than a distal end of the housing, exposed outwardly of the housing on an outer surface thereof, and rotatable in unison with the elongated member around the axis of rotation. The elongated member is defined by a sheath or is defined by a shaft.

Another aspect of the disclosed technology is directed to a treatment tool comprises a housing. An elongated member having respective proximal and distal ends. The elongated member is configured to be attached to the housing via the proximal end. The elongated member rotates around an axis of rotation with respect to the housing. An end effector is configured to be attached to the distal-end of the elongated member and rotates in unison with the elongated member around the axis. A locking member is configured to be attached to the housing so as to engage with the elongated member for restraining rotation of the elongated member around the axis. A manipulating member is attached to the housing and moves with respect to the housing for switching from an engaged position to a disengaged position and vice versa. The locking member and the elongated member are capable to engage with or to disengage from one another.

The manipulating member moves between a locking position in the engaged position and an unlocking position in the disengaged position. The manipulating member moves from the unlocking position to the locking position by a first force applied thereto when the manipulating member is in the unlocking position. The manipulating member remains in the locking position even if the manipulating member is released from the first force applied thereto. The manipulating member moves from the locking position to the unlocking position by a second force applied thereto when the manipulating member is in the locking position. The manipulating member moves between a locking position in the engaged position and an unlocked position in the disengaged position. The manipulating member moves from the unlocking position to the locking position by a first force applied thereto when the manipulating member is in the unlocking position. The manipulating member moves from the locking position to the unlocking position by being released from the first force applied thereto.

While the embodiments, etc. have been described hereinbefore, the present disclosure is not limited to the embodiments and the modifications. Various changes and modifications may be made therein without departing from the scope of the disclosure.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless other-wise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment tool comprising:
a housing having a side surface facing in a widthwise direction thereof;
an elongated member having respective proximal and distal ends wherein the elongated member is configured to be attached to the housing via the proximal end, the elongated member being rotatable around an axis of rotation with respect to the housing;
an end effector configured to be attached to the distal-end of the elongated member and being rotatable in unison with the elongated member around the axis of rotation;
a slidable locking member configured to be attached to the housing so as to be engageable with the elongated member for restraining rotation of the elongated member around the axis of rotation with respect to the housing; and
two manipulating members configured to be attached to the housing and being movable with respect to the housing in a first direction along the axis of rotation, a second direction toward the axis of rotation, or a third direction along the side surface and transverse to the axis of rotation, for switching from an engaged position to a disengaged position and vice versa and wherein in the engaged position, the slidable locking member and the elongated member engage with one another and in the disengaged position, the slidable locking member and the elongated member disengage from one another, a first of the two manipulating members disposed on an opposite longitudinal end of the slidable locking member from a second of the two manipulating members, the two manipulating members extending substantially parallel to each other.

2. The treatment tool of claim 1,
wherein the housing includes a grip attached thereto and extending downwardly in a direction transverse to the axis of rotation and the widthwise direction; and
the manipulating members are disposed on the side surface of the housing and move in the first direction, the second direction, or the third direction upon switching between the engaged position and the disengaged position.

3. The treatment tool of claim 2,
wherein while the housing is being held by a hand, the palm and the thumb of the hand are held against the grip from a proximal-end side, and the manipulating members are positioned in a range where the thumb can abut against the manipulating members.

4. The treatment tool of claim 2, wherein the manipulating members cause the slidable locking member and the elongated member to switch from the disengaged position to the engaged position by moving from a distal-end side of the treatment tool toward a proximal-end side of the treatment tool in the first direction, moving toward the axis of rotation in the second direction, or moving toward a side where the grip is positioned in the third direction.

5. The treatment tool of claim 1, wherein the manipulating members move between a locked position in which the slidable locking member and the elongated member engage with one another and an unlocked position in which the slidable locking member and the elongated member disengage from one another;
the manipulating members move to the locked position by a first manipulating force that is applied thereto when the manipulating members are in the unlocked position;
the manipulating members remain in the locked position even if the manipulating members are released from the manipulating force applied thereto when the manipulating members have been moved to the locked position by the first manipulating force; and
the manipulating members move to the unlocked position by a second manipulating force applied thereto when the manipulating members are in the locked position.

6. The treatment tool of claim 1,
wherein the end effector is capable of being bent and/or curved with respect to the axis of rotation.

7. The treatment tool of claim 1,
wherein the elongated member has a rotary member coupled to the housing from a distal end of the housing, exposed outwardly of the housing, and rotates in unison with the elongated member around the axis of rotation.

8. The treatment tool of claim 1,
wherein the elongated member is inserted into the housing and wherein the elongated member includes a rotary member disposed more closely to a proximal-end side than a distal end of the housing, exposed outwardly of the housing on an outer surface thereof, and rotatable in unison with the elongated member around the axis of rotation.

9. The treatment tool of claim 1, wherein the elongated member is defined by a sheath.

10. The treatment tool of claim 1, wherein the elongated member is defined by a shaft.

11. A treatment tool comprising:
a housing;
an elongated member having respective proximal and distal ends wherein the elongated member is configured to be attached to the housing via the proximal end, the elongated member rotates around an axis of rotation with respect to the housing;
an end effector configured to be attached to the distal-end of the elongated member and rotates in unison with the elongated member around the axis; a slidable locking member configured to be attached to the housing so as to engage with the elongated member for restraining rotation of the elongated member around the axis; and
two manipulating members each attached to the housing and moving with respect to the housing for switching from an engaged position to a disengaged position and vice versa and wherein the slidable locking member and the elongated member are capable to engage with or to disengage from one another, a first of the two manipulating members disposed on an opposite longitudinal end of the slidable locking member from a second of the two manipulating members, the two manipulating members extending substantially parallel to each other;
wherein the manipulating members move between a locking position in the engaged position and an unlocking position in the disengaged position,
the manipulating members move from the unlocking position to the locking position by a first force applied thereto when the manipulating members are in the unlocking position;
the manipulating members remain in the locking position even if the manipulating members are released from the first force applied thereto; and
the manipulating members move from the locking position to the unlocking position by a second force applied thereto when the manipulating members are in the locking position.

12. A treatment tool comprising:
a housing having a side surface facing in a widthwise direction thereof;
an elongated member having respective proximal and distal ends wherein the elongated member is configured to be attached to the housing via the proximal end, the elongated member being rotatable around an axis of rotation with respect to the housing;
an end effector configured to be attached to the distal-end of the elongated member and being rotatable in unison with the elongated member around the axis of rotation;
a slidable locking member configured to be attached to the housing so as to be engageable with the elongated member for restraining rotation of the elongated member around the axis of rotation with respect to the housing; and
a manipulating member configured to be attached to the housing and being movable with respect to the housing in a first direction along the axis of rotation, a second direction toward the axis of rotation, or a third direction along the side surface and transverse to the axis of rotation, for switching from an engaged position to a disengaged position and vice versa and wherein in the engaged position, the slidable locking member and the elongated member engage with one another via direct contact to one another and in the disengaged position, the slide member and the elongated member disengage from one another.

* * * * *